(12) United States Patent
Mathies

(10) Patent No.: US 9,649,190 B2
(45) Date of Patent: May 16, 2017

(54) METHOD FOR REPAIR OF LIGAMENT OR TENDON

(71) Applicant: TRB Chemedica International S.A., Geneva (CH)

(72) Inventor: Burkhard Mathies, Givrins (CH)

(73) Assignee: TRB Chemedica International S.A., Geneva (CH)

(*) Notice: Subject to any disclaimer, the term of this patent is extended or adjusted under 35 U.S.C. 154(b) by 0 days.

(21) Appl. No.: 14/386,756

(22) PCT Filed: Mar. 22, 2013

(86) PCT No.: PCT/EP2013/056045
§ 371 (c)(1),
(2) Date: Sep. 19, 2014

(87) PCT Pub. No.: WO2013/139955
PCT Pub. Date: Sep. 26, 2013

(65) Prior Publication Data
US 2015/0045887 A1    Feb. 12, 2015

Related U.S. Application Data

(60) Provisional application No. 61/613,998, filed on Mar. 22, 2012.

(51) Int. Cl.
*A61F 2/08* (2006.01)
*A61L 27/24* (2006.01)
(Continued)

(52) U.S. Cl.
CPC .............. *A61F 2/08* (2013.01); *A61F 2/0063* (2013.01); *A61L 27/20* (2013.01); *A61L 27/24* (2013.01);
(Continued)

(58) Field of Classification Search
CPC .. A61F 2/0063; A61F 2002/0068; A61F 2/08; A61B 17/1146
See application file for complete search history.

(56) References Cited

U.S. PATENT DOCUMENTS 3,797,047 A    3/1974 Pillet
4,187,558 A    2/1980 Dahlen et al.
(Continued)

FOREIGN PATENT DOCUMENTS

EP    1 319 415 A1    6/2003
JP    2003-010308 A    1/2003
(Continued)

OTHER PUBLICATIONS

Aspinall, *Polysaccharides*, Pergamon Press Ltd., Headington Hill Hall, Oxford, 1970, 14 pages.
(Continued)

*Primary Examiner* — Katrina Stransky
*Assistant Examiner* — Daniel Bissing
(74) *Attorney, Agent, or Firm* — Seed IP Law Group LLP

(57) ABSTRACT

This invention relates to a method for repair of a ligament and/or tendon in a patient comprising applying a patch to said ligament or tendon, wherein the patch is flexible, and bio-compatible and comprises a support layer and a matrix layer.

19 Claims, 12 Drawing Sheets

(51) Int. Cl.
*A61L 27/26* (2006.01)
*A61L 27/48* (2006.01)
*A61L 27/54* (2006.01)
*A61F 2/00* (2006.01)
*A61L 27/20* (2006.01)
*A61L 27/36* (2006.01)
*A61L 27/56* (2006.01)

(52) U.S. Cl.
CPC ............. *A61L 27/26* (2013.01); *A61L 27/362* (2013.01); *A61L 27/3604* (2013.01); *A61L 27/3662* (2013.01); *A61L 27/48* (2013.01); *A61L 27/54* (2013.01); *A61L 27/56* (2013.01); *A61F 2210/0004* (2013.01); *A61L 2300/412* (2013.01); *A61L 2430/10* (2013.01)

(56) References Cited

U.S. PATENT DOCUMENTS

| | | | |
|---|---|---|---|
| 4,483,023 A | | 11/1984 | Hoffman, Jr. et al. |
| 4,585,458 A | * | 4/1986 | Kurland ............. A61B 17/1146 128/899 |
| 4,610,688 A | | 9/1986 | Silvestrini et al. |
| 4,792,336 A | | 12/1988 | Hlavacek et al. |
| 5,061,283 A | | 10/1991 | Silvestrini |
| 5,245,098 A | | 9/1993 | Summers et al. |
| 5,263,984 A | | 11/1993 | Li et al. |
| 6,737,072 B1 | | 5/2004 | Angele et al. |
| 6,773,723 B1 | | 8/2004 | Spiro et al. |
| 6,964,685 B2 | | 11/2005 | Murray et al. |
| 7,252,832 B1 | | 8/2007 | Stone et al. |
| 8,080,260 B2 | * | 12/2011 | Derwin ..................... A61F 2/08 424/423 |
| 2002/0123805 A1 | | 9/2002 | Murray et al. |
| 2003/0133967 A1 | | 7/2003 | Ruszczak et al. |
| 2003/0143207 A1 | | 7/2003 | Livesey et al. |
| 2004/0059416 A1 | | 3/2004 | Murray et al. |
| 2005/0226936 A1 | * | 10/2005 | Agerup ................... A61L 15/20 424/489 |
| 2005/0261736 A1 | | 11/2005 | Murray et al. |
| 2007/0141101 A1 | * | 6/2007 | Nugent ............. A61K 47/4823 424/423 |
| 2008/0031923 A1 | | 2/2008 | Murray et al. |
| 2008/0154370 A1 | * | 6/2008 | Mathies ............... A61F 2/30756 623/14.12 |
| 2009/0204227 A1 | | 8/2009 | Derwin et al. |
| 2010/0040685 A1 | | 2/2010 | Lee et al. |
| 2010/0292791 A1 | * | 11/2010 | Lu .......................... A61K 38/18 623/13.12 |
| 2012/0070466 A1 | * | 3/2012 | Harris ..................... A61K 8/02 424/400 |

FOREIGN PATENT DOCUMENTS

| | | |
|---|---|---|
| JP | 2003-525705 A | 9/2003 |
| JP | 2004-507472 A | 3/2004 |
| JP | 2005-506121 A | 3/2005 |
| JP | 2012-515035 A | 7/2012 |
| WO | 95/02550 A1 | 1/1995 |
| WO | 2007/087353 A2 | 8/2007 |
| WO | 2010/082138 A2 | 7/2010 |
| WO | 2010/083487 A1 | 7/2010 |

OTHER PUBLICATIONS

Dodgson et al., "Metabolism of Acidic Glycosaminoglycans (Mucopolysaccharides)," in *Carbohydrate Metabolism and Its Disorders*, Dickens et al. (eds.), vol. 1, Academic Press, London and New York, 1968, pp. 169-212, 30 pages.

* cited by examiner

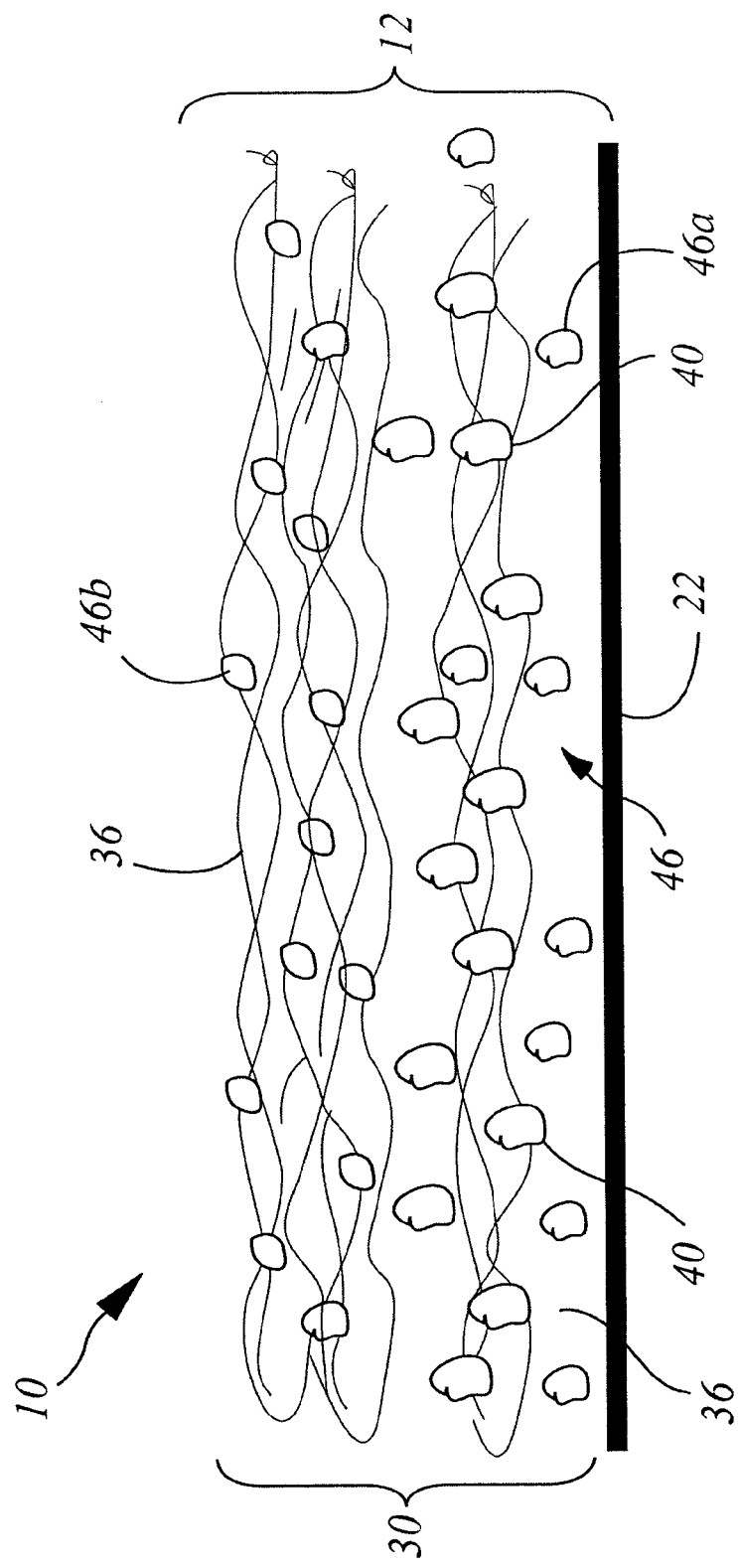
Fig. 1.B

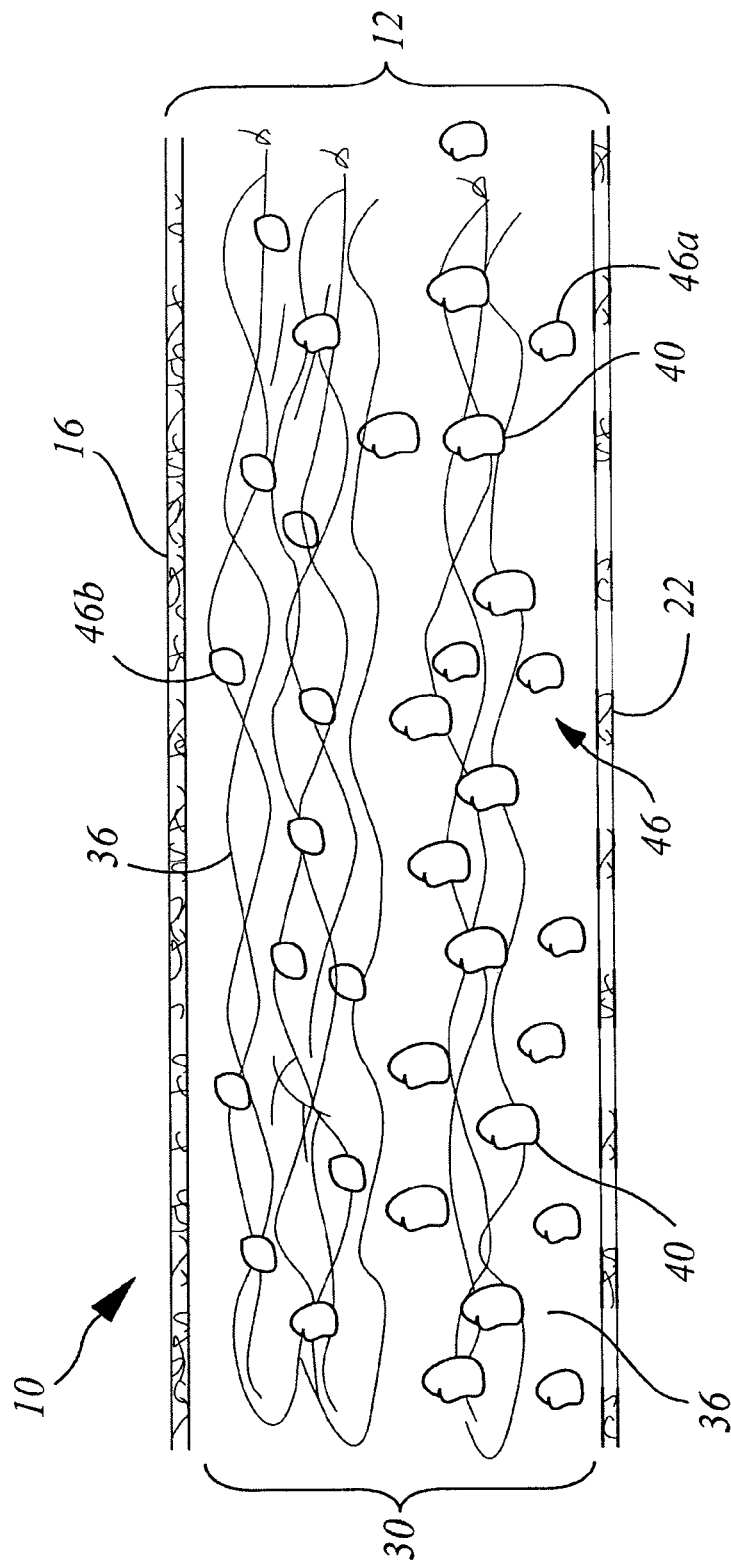
Fig. 2.A

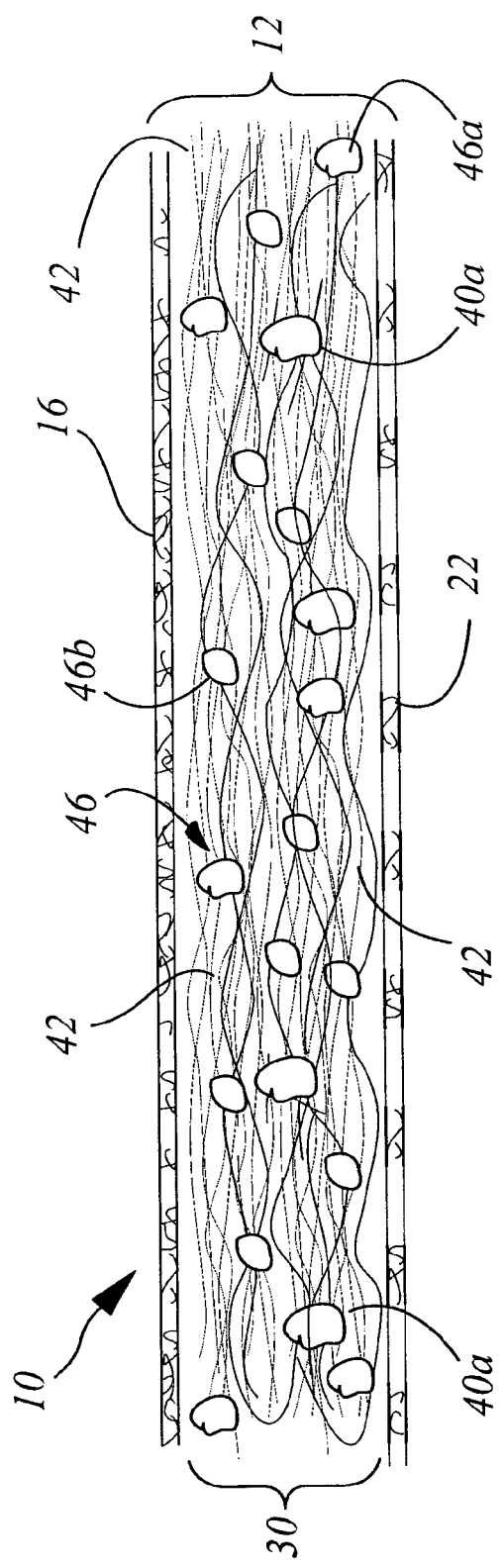
Fig. 2.B

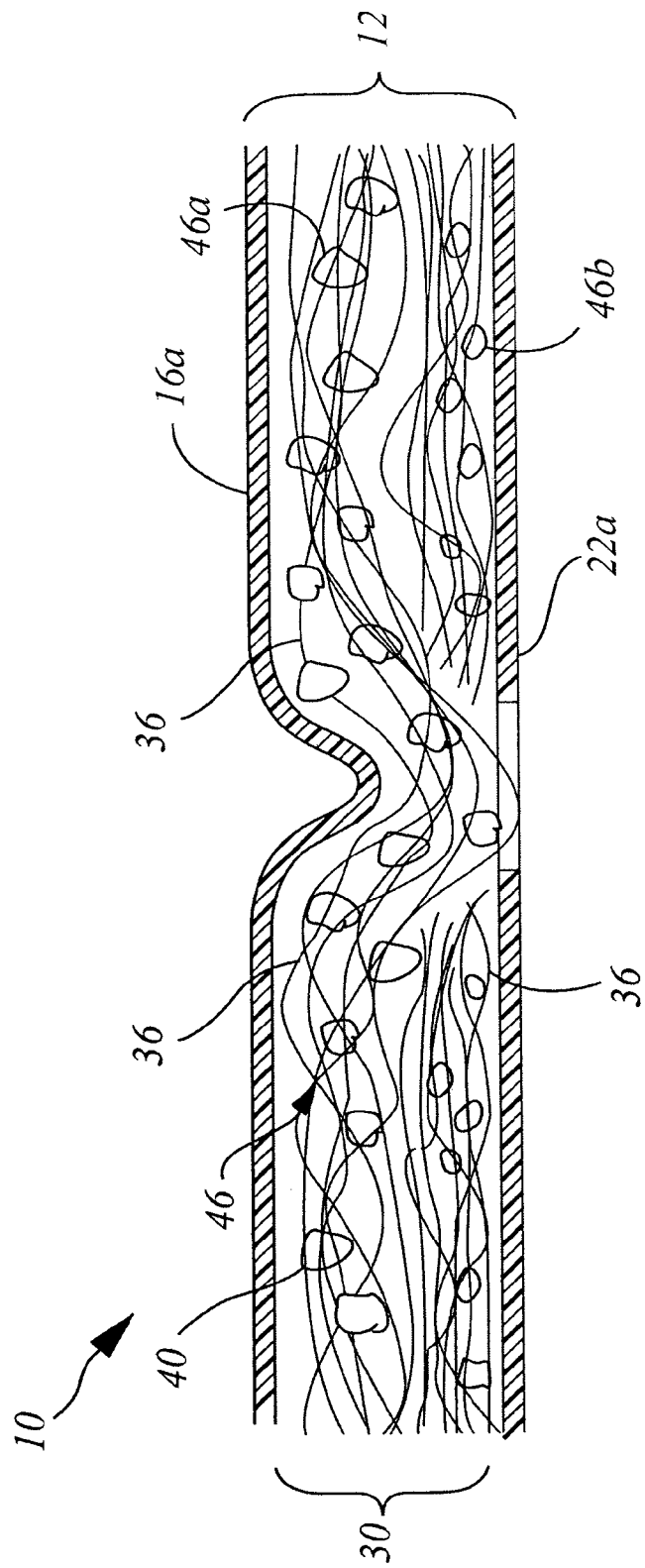
Fig. 2.C

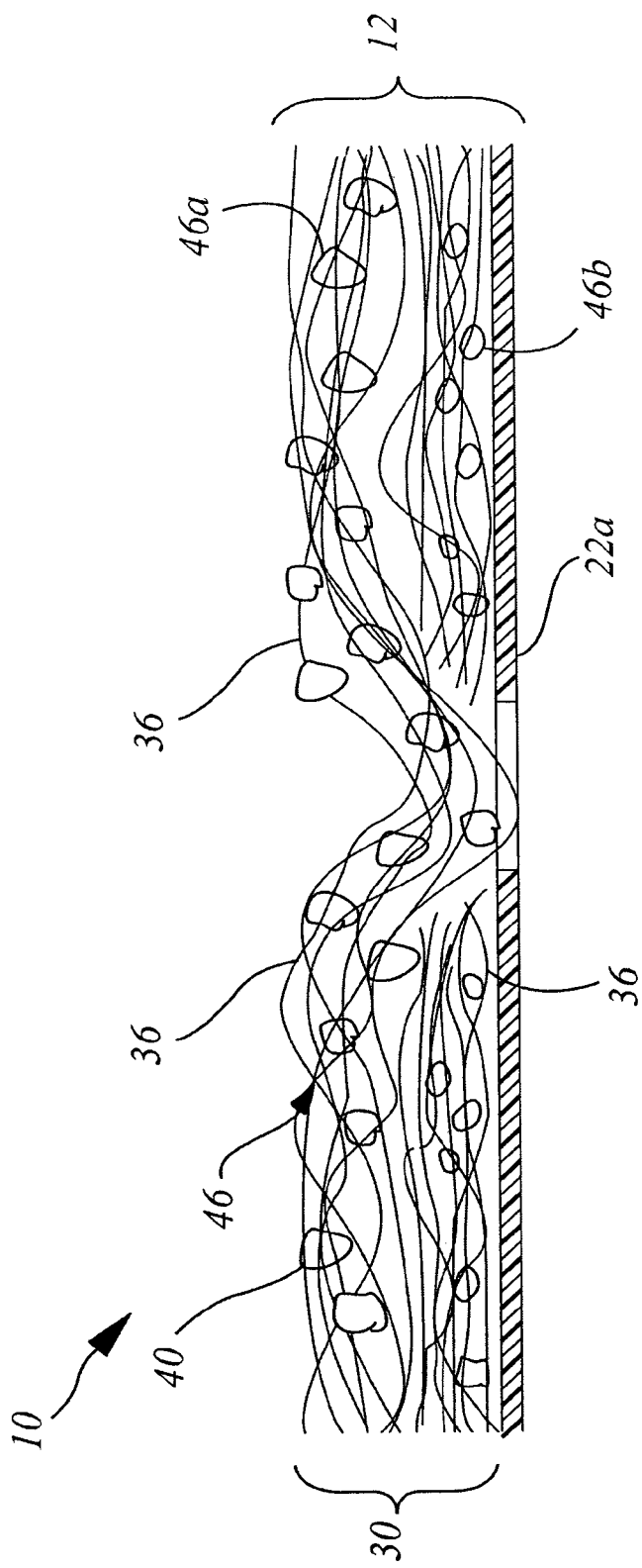
Fig. 2.D

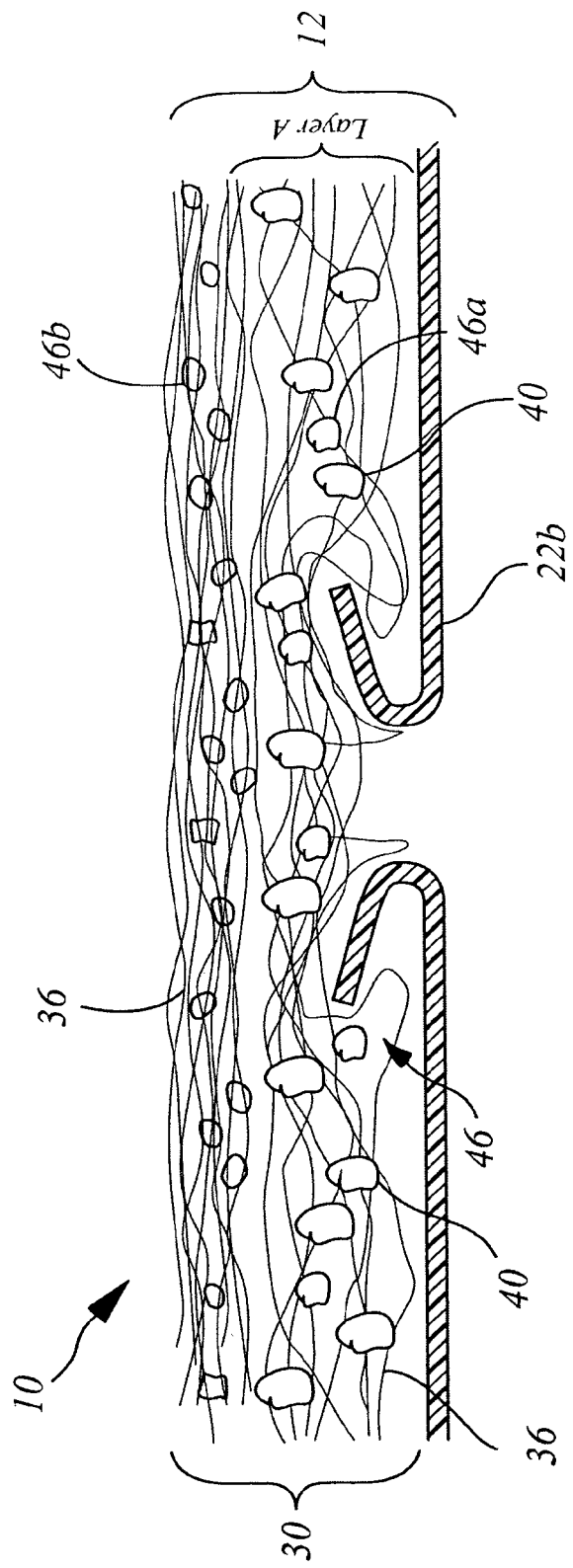
Fig. 2.E

METHOD FOR REPAIR OF LIGAMENT OR TENDON

FIELD OF THE INVENTION

This invention lies in the field of medical care devices and relates to methods for repair of a ligament or tendon comprising the use of a ligament or tendon repair patch.

BACKGROUND

Ligaments are specialized connective soft tissues which connect different organs or tissues and attach bone to bone. In the latter case, ligaments provide stability to joints by being flexible enough to allow natural movement of the bones yet also are strong and inextensible to prevent resistance to applied forces. Tendons connect muscle to bone and are capable of withstanding tension. In addition, tendons passively modulate forces during locomotion, providing additional stability with no active work. Their elastic properties allow tendons to store and recover energy at high efficiency. In tendons and ligaments, bundles of collagen fibers are embedded in a connecting matrix made of proteoglycans components. These bundles of collagen fibers provide the load carrying elements. In tendons, the collagen fibers are arranged in nearly parallel formation, thus enabling them to withstand high unidirectional loads. In ligaments, the collagen fibers are arranged in a less parallel formation, thereby enabling them to withstand predominant tensile stresses in one direction and smaller stresses in other directions.

Every year, hundreds of thousands of people sprain, tear, or rupture ligaments in particular in the knee, shoulder, and ankle or suffer from injuries to tendons of the upper and lower extremities, in particular in the shoulder, knee, foot, and ankle. One such ligament often affected by these type of injuries is the anterior cruciate ligament (ACL) of the knee. The ACL serves as a primary stabilizer of anterior tibial translation and as a secondary stabilizer of valgus-varus knee angulation, and is often susceptible to rupture or tear resulting from a flexion-rotation-valgus force associated with sports injuries and traffic accidents. Ruptures or tears often result in: severe limitations in mobility; pain and discomfort; and an inability to participate in sports and exercise. More than 200,000 people in the U.S. alone tear or rupture their ACL each year, leading to costs of approximately $3 billion for ACL reconstructive surgery and extensive rehabilitation.

It is widely known that the ACL has poor healing capabilities. Total surgical replacement and reconstruction are required when the ACL suffers a significant tear or rupture resulting in joint instability. The most common practice is to reconstruct a torn ACL by substituting the torn ligament with the patient's own tissue, also known as an autograft. Other options for substitute ligaments include donor tissues from another organism, also known as allografts, as well as synthetic grafts. However, there are various problems associated with these treatments.

Surgeons have considered ligament constructs comprising collagen fibers, biodegradable polymers and composites thereof. Collagen scaffolds for ACL reconstruction seeded with fibroblasts from ACL and skin are described for example in the international patent application WO 95/2550. U.S. Patent Application No. 20020123805 by Murray, et al. describes the use of a three-dimensional scaffold composition which includes an inductive core made of collagen or other material, for repairing a ruptured anterior cruciate ligament (ACL) and a method for attaching the composition to the ruptured anterior cruciate ligament (See also U.S. Patent Application No. 20040059416). WO 2007/087353 discloses three-dimensional scaffolds for repairing torn or ruptured ligaments. The scaffold may be made of protein, and may be pretreated with a repair material such as a hydrogel or collagen. U.S. Patent Application No. 20080031923 by Murray, et al. describes preparation of a collagen gel and a collagen-MATRIGEL™ gel which is applied to a torn ligament for repair of the ligament. These collagen matrices are mostly monocomponent devices.

A number of multicomponent ligament prosthesis have been described (see, e.g. U.S. Pat. Nos. 3,797,047; 4,187,558; 4,483,023, 4,610,688 and 4,792,336). U.S. Pat. No. 4,792,336 discloses a device with an absorbable component comprising a glycolic or lactic acid ester linkage, and the remainder of the device comprising a non-absorbable component. The device includes a plurality of fibers comprising the absorbable component which can be used as a flat braid in the repair of a ligament or tendon. The required tensile strength is obtained by increasing the final braid denier. U.S. Pat. No. 5,061,283 discloses a bicomponent device comprising polyethylene terepthalate and a polyester/polyether block copolymer for use in ligament repair. U.S. Pat. No. 5,263,984 describes prosthetic ligament which is a composite of two densities of bioresorbable filaments. However, there is still need in the art for a method of ligament and tendon repair that enhances cell ingrowth and metaplastic transformation of the graft tissue to obtain a functional strong neo-ligament/-tendon.

SUMMARY OF THE INVENTION

The present invention provides for a method for repair, regeneration or reconstruction of a ligament or tendon in ligament/tendon injury, e.g. articular ligament injury, which comprises implanting at the site of the damaged ligament/tendon area a biocompatible repair patch, which supports ingrowth of cells and formation of new tissue.

The present invention relates to a method for repair of a ligament or tendon in a patient comprising the step of applying a patch to said ligament or tendon, wherein the patch is flexible, and bio-compatible and comprises a support layer comprising collagen, and a matrix layer comprising collagen and hyaluronic acid.

In various embodiments of this method, the support layer is a collagen sheet layer.

In certain embodiments of this method, the support layer comprises porcine, bovine or equine pericard membrane or porcine split skin.

In some embodiments of this method, the support layer is cell porous.

In various embodiments of this method, the support layer comprises a dried porcine split skin (Xenoderm) layer.

In some embodiments of this method, the matrix layer is a porous collagenous layer.

In certain embodiments of this method, the matrix layer comprises a collagen fiber matrix.

In certain embodiments of this method, the collagen of the matrix layer comprises collagen of porcine, equine, bovine or vegetal origin.

In some embodiments of this method, the hyaluronic acid of the matrix layer comprises natural, non-human hyaluronic acid.

In various embodiments of the method, the natural hyaluronic acid of the matrix layer comprises natural, non-human hyaluronic acid from a bacterial fermentation source.

In certain embodiments of the method, the matrix comprises hyaluronic acid in form of fibers, powder, gel or cream suspension.

In further embodiments of the method, the matrix layer is a porous collagenous composite pad interspersed with collagen fibers and natural hyaluronic acid dispersed into the vacant spaces of the collagen fibers.

In some embodiments of the method, the matrix layer further comprises one or more compounds selected from analgesics, anti-inflammatory agents, antibiotics, and agents promoting ligament or tendon regeneration.

In certain embodiments of the method, the agents promoting ligament or tendon regeneration are selected from the group consisting of: growth factors, Diacerein, Rhein, chitosan and its derivatives, platelet rich plasma (PRP), and poly-lactic acid. The growth factors may be selected from the group consisting of, but not limited to, fibroblast growth factor (FGF), transforming growth factor (TGF-β1), basic fibroblast growth factor (bFGF), Hepatocyte growth factor (HGF), blood, bone morphogenetic proteins (BMPs), osteoinductive factor (IFO), fibronectin (FN), endothelial cell growth factor (ECGF), cementum attachment extracts (CAE), ketanserin, human growth hormone (HGH), animal growth hormones, epidermal growth factor (EGF), human alpha thrombin, insulin-like growth factor (IGF-I), platelet derived growth factors (PDGF, PDGF-AB), periodontal ligament chemotactic factor (PDLGF), and somatotropin.

In another embodiment, the agents include living cells, for example fibroblasts and/or stem cells. When stem cells are used, in certain embodiments human embryonic stem cells are excluded.

In further embodiments of the method, the patch further comprises a third layer, which is disposed on the matrix layer such that the matrix layer is sandwiched between the support layer and the third layer.

In some embodiments of the method, the third layer is a collagen sheet layer.

In certain embodiments of the method, the third layer comprises porcine, bovine, or equine pericard membrane or porcine split skin.

In further embodiments of the method, the third layer is cell porous.

In certain embodiments of the method, the third layer comprises a dried porcine split skin (Xenoderm) layer.

In some embodiments of the method, the patch has a thickness of between 0.5-2 mm.

In further embodiments of the method, the ligament or tendon is selected from the group of ligaments connected to the head, neck, spine, thorax, pelvis, in the upper and lower extremities, e.g., shoulder, elbow, wrist, hand, hip, knee, foot, and ankle, and the group of tendons in the upper and lower extremities, in particular shoulder, elbow, hands, hip, knee, feet, and ankle.

In certain embodiments of the method, the ligament is selected from the group consisting of cricothyroid ligament, periodontal ligament, suspensory ligament of the lens, suspensory ligament of the breast, anterior sacroiliac ligament, posterior sacroiliac ligament, sacrotuberous ligament, sacrospinous ligament, inferior pubic ligament, superior pubic ligament, suspensory ligament of the penis, palmar radiocarpal ligament, dorsal radiocarpal ligament, ulnar collateral ligament, radial collateral ligament, acromio-clavicular ligament, coraco-clavicular ligament, cruciate ligament, anterior cruciate ligament (ACL), lateral collateral ligament (LCL), posterior cruciate ligament (PCL), medial collateral ligament (MCL), and patellar ligament.

In various embodiments of the method, the tendon is selected from the group of tendons consisting, but not being limited to, tendons connected to lower and upper extremities, tendons in the thoracic and abdominal area, spine, comprising head and neck, tendons in the hip and pelvic area, knee, foot, and ankle, and quadriceps tendon, patellar tendon, tibialis ant. and post. tendons, peroneal tendons, Achilles tendon, extensor, flexor, abductor and adductor tendons of the foot and toes, tendons in the shoulder, elbow, and hand, rotator cuff tendons, subscapularis tendon, deltoid and pectoralis tendons, biceps brachii tendon, triceps brachii tendon, extensor, flexor, and abductor and adductor tendons of the hand and fingers. Also comprised are any further ligaments and tendons.

In some embodiments of the method, the patient is afflicted by a disorder affecting a ligament or tendon comprising inflammation, autoimmune disease, infection, stress, strain, rupture, sprain, avulsion, overstretching, or tearing of the ligament or tendon.

BRIEF DESCRIPTION OF THE DRAWINGS

FIG. 2 shows a cross-sectional side view of certain embodiments of the sterilizable, flexible laminate ligament or tendon repair patch comprising two or three layers for the method of the present invention, in 2A detailing the composition of the matrix of the patch wherein the collagen and the hyaluronic acid are disposed as fibers, in 2B detailing the composition of the inner matrix of the patch, wherein the collagen is disposed as fibers and the hyaluronic acid is disposed as a cream suspension or as a viscoelastic solution, in 2C showing a support and a third layer both having a mechanical stabilizing feature in each layer, in 2D showing an embodiment having a support layer with a mechanical stabilizing feature, and in 2E showing an embodiment wherein the support layer has complex mechanical stabilizing features in it.

FIG. 6 shows progenitor cells (60) that migrate from fibrin-blood clot (59) into damaged tendon/ligament (61) and into the repair patch matrix (12) differentiating into Fibroblasts (62).

DETAILED DESCRIPTION

Figure 1A:
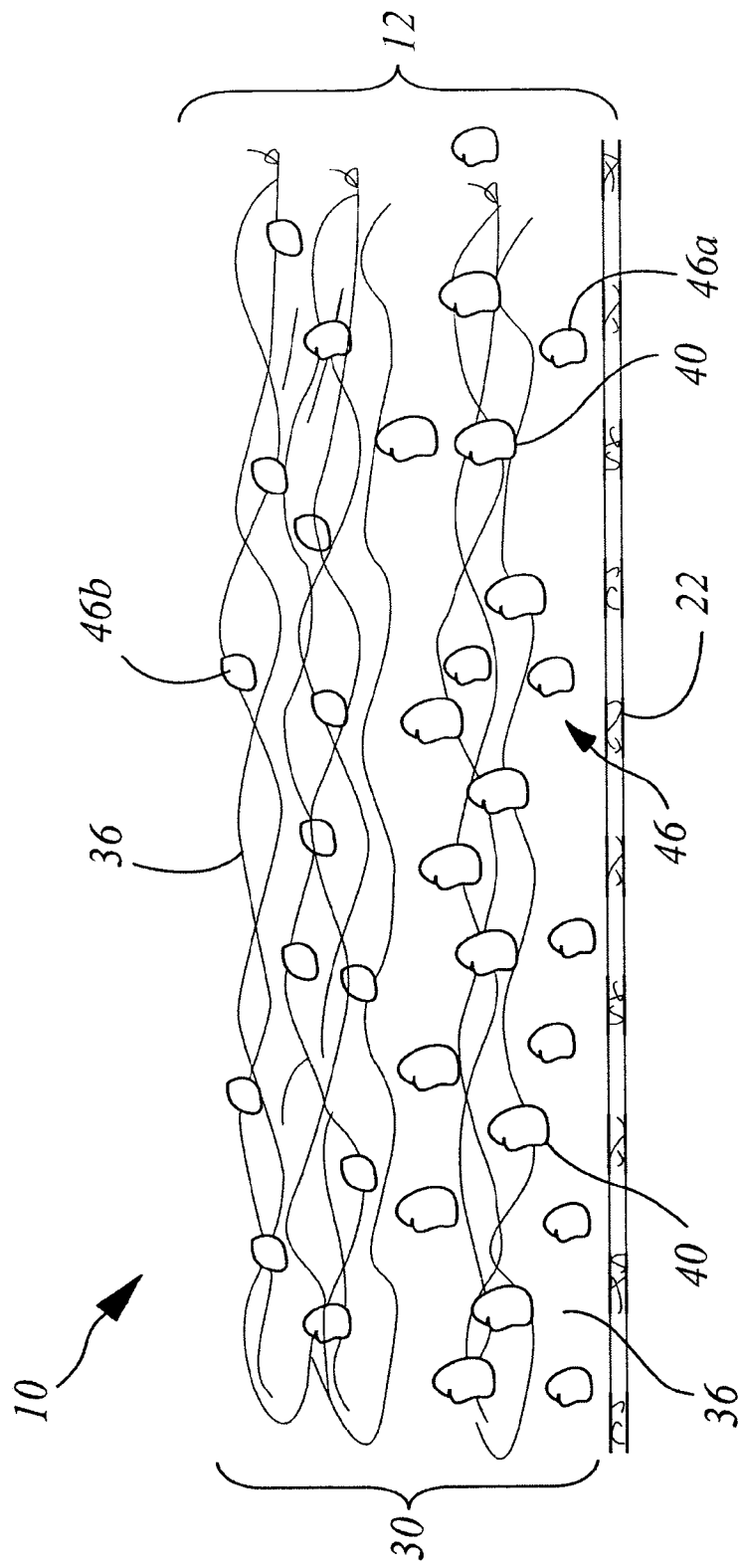
FIG. 1 shows a cross-sectional view of a sterilizable, flexible laminate ligament or tendon repair patch 10 comprising two layers, a support layer 22 and a matrix layer 30, forming a laminate 12 for the method of the present invention, detailing the composition of the matrix of the patch wherein the collagen and the hyaluronic acid are disposed as fibers and the support layer is porous (FIG. 1A) or non-porous (FIG. 1B).
Figure 3:
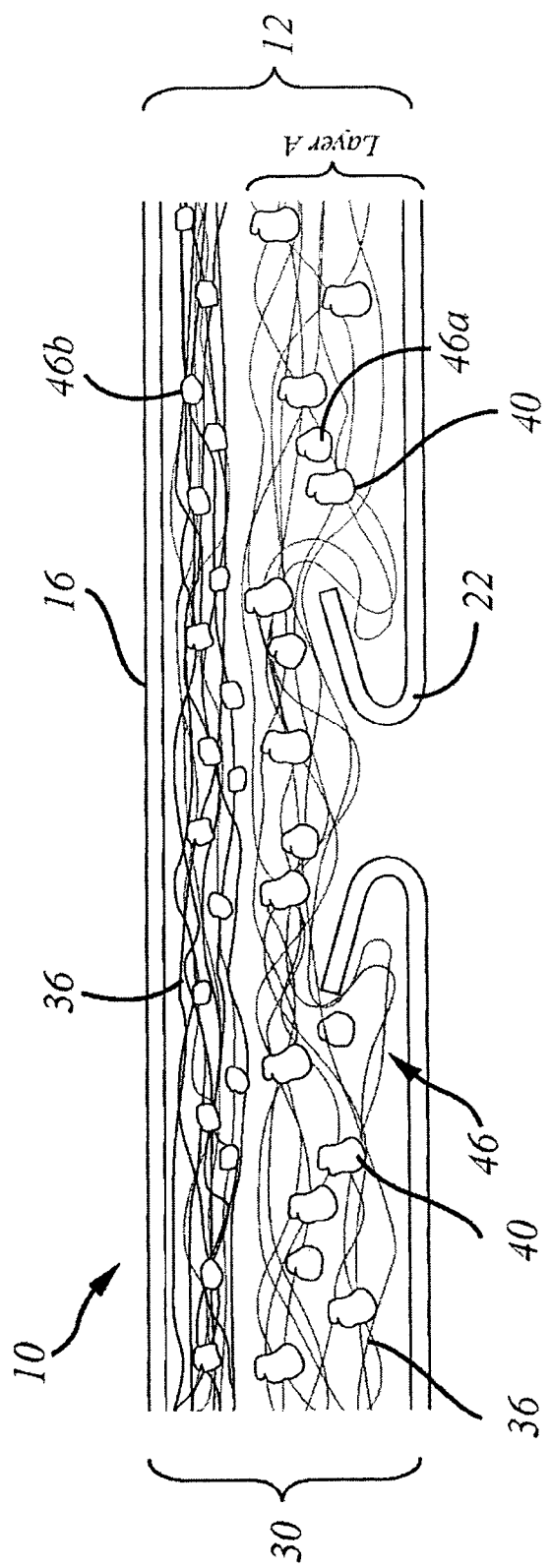
FIG. 3 shows a cross-sectional side view of an embodiment of the sterilizable, flexible laminate ligament or tendon repair patch comprising a support, matrix and third layer for the method of the present invention. Layer 22 is a porous support layer, wherein layer 16 is optionally occlusive or porous. The matrix configuration resembles that highlighted in FIG. 2E.

One of the problems faced in the field of ligament and tendon repair is how to promote regeneration of ligament or tendon tissue at the site of ligament or tendon injury.

The term "ligament or tendon injury", as used herein refers to a chronic or acute condition affecting the ligament or tendon. Examples of ligament or tendon injuries are inflammation, autoimmune disease, infection, stress, strain, rupture, sprain, avulsion, overstretching, or tearing of the ligament or tendon.

It is an object of the present invention to provide a method for ligament or tendon repair which leads to the restoration of a functional, anatomic ligament or tendon tissue.

The term "repair of a ligament or tendon" as used in the present invention means that the ligament or tendon injury, the chronic or acute condition affecting the ligament or tendon, is healed or at least alleviated so that the function of the ligament or tendon is at least partially restored or completely restored.

A drawback of known absorbable prosthesises based solely on synthetic, non-collagenous polymers is that the prosthesises cannot exhibit the beneficial lesion-healing properties of biopolymers such as collagen. It is well known that injury-healing cells such as fibroblasts have a special affinity for collagen and certain other biopolymers. This property is termed the chemotactic effect of collagen.

The invention is based on the inventor's surprising finding that a flexible and bio-compatible patch comprising a support layer comprising collagen and a matrix layer comprising collagen and hyaluronic acid can be advantageously used in the repair of ligaments and tendons and may in—conjunction with subchondral blood and its MSC's or added fibroblasts cell culture and fibrin glue—present a biofactory that strongly enhances the ligament repair process or the transformation of implanted ligament graft structure into a neo-ligament. The same also applies for the use of the patch in tendon repair.

Thus, the present invention relates to methods for repair of a ligament or tendon in a subject, such as a human patient, comprising applying such patch to a ligament or tendon of said subject.

Accordingly, in certain embodiments the present invention relates to a method for repair of a ligament in a subject comprising applying such patch to a ligament of said subject.

Furthermore, in various embodiments the present invention relates to a method for repair of a tendon in a subject comprising applying such patch to a tendon of said subject.

The subject may be a human patient.

The claimed method is advantageous, as it promotes faster regeneration of injured ligaments and tendons or ligament and tendon grafts, hence provide benefit due to a faster functional and anatomic recovery of the patients.

Furthermore, the claimed method is advantageous, as the ligament or tendon repair method does not require cell culture as do prior art methods. Nevertheless, in some embodiments the method may comprise the use of a repair patch which comprises cultivated cells for further enhancing the ligament or tendon repair.

In certain embodiments, the method described herein does not propagate the formation of fibrous tissue at the injury site.

The present invention thus relates to methods for repair of a ligament or tendon in a patient comprising the step of applying a patch to said ligament or tendon, wherein the patch is flexible, and bio-compatible and comprises a support layer comprising collagen, and a matrix layer comprising collagen and hyaluronic acid.

The patch is biologically acceptable, compatible and easy to use. It has a relatively fast setting time and possesses required adhesive and cohesive properties. It is non-toxic and non-rigid. Additionally, it does not interfere with the healing process or formation of new ligament or tendon tissue, and does not promote the formation of other interfering or undesirable tissues.

While this invention is described for use in humans, in certain embodiments the method of the present invention described herein may be applied to animals, including but not limited to mammals and birds. In various embodiments, the ligament or tendon repair method is applied to mammals, such as dog, cat, horse, cow, sheep, pig, monkey, ape, chimpanzee, human and other mammals in which one may want to repair an injured ligament or tendon. However, this list is not exhaustive, and one could easily use this repair patch in any animal.

The term "treating", "treatment", "repair", "repairing", "heal" or "healing" of a condition described herein refers to executing a protocol, which may include administering one or more drugs to a subject (human or otherwise) and/or performing surgery (minimally invasive or otherwise) on a patient, in an effort to alleviate signs or symptoms of the conditions described herein, for example the severing of or other type of injury to a ligament or tendon. The terms also include the prevention of such a condition, for example by preventing reoccurrence. Reoccurrence may happen when a severed or injured ligament or tendon does not heal properly and leaves the joint unstable and painful. In addition, prevention can include inhibiting the formation of scar tissue and/or adhesions that sometimes occur to a ligament during healing from another type of injury. In addition, "treating" or "treatment" does not require complete alleviation of signs or symptoms and does not require a cure.

In certain embodiments, the repair patch is made of layers comprising natural polymers and/or synthetic polymers. In various embodiments, the collagen of the support layer and/or matrix layer comprises collagen of animal or vegetal origin.

In certain embodiments, the collagen of the support layer and/or matrix layer may be obtained from animals, preferably mammals, such as dogs, cats, horses, cows, sheep, pigs, monkeys, apes, chimpanzees, or humans. In certain embodiments, an autologous repair patch is employed, wherein the collagen is prepared from the subject which is treated with the repair patch for ligament or tendon repair. Among these embodiments, collagen from a human patient may be isolated to prepare the patch which is later implanted into the patient for ligament or tendon repair.

Sources of collagen are collagenous tissues, which in mammals include skin (hide), tendon, intestine, fascia lata, pericardium, and dura mater. One possibility to obtain collagen is the use of the submucosa layer of the small intestine. Collagen layer may be prepared from dentin and cortical bone, for example from porcine or bovine dentin and cortical bone.

For example, the collagen can be type I, II, III, IV, V, IX or X. Preferably the collagen is type I.

Type I collagen is the predominant component of the extracellular matrix for the human anterior cruciate ligament and provides an example of choice for manufacturing a bioengineered scaffold. Collagen occurs predominantly in a fibrous form, allowing design of materials with very different mechanical properties by altering the volume fraction, fiber orientation, and degree of cross-linking of the collagen. The biologic properties of cell infiltration rate and scaffold degradation may also be altered by varying the pore size, degree of cross-linking, and the use of additional compounds, such as glycosaminoglycans, growth factors, and cytokines. In certain embodiments, the collagen-based layers disclosed herein are manufactured from a patient's own skin, thus minimizing the antigenicity of the implant.

Cytokines are small cell-signaling protein molecules that are secreted by numerous cells. Cytokines can be proteins, peptides, or glycoproteins. Based on their presumed function, cell of secretion, or target of action, cytokines have been classed as lymphokines, interleukins, and chemokines. The group of cytokines includes, but is not limited to IL-2, IL-4, interferon gamma (IFN-γ), TGF-β, IL-10, IL-13, erythropoietin (EPO), thrombopoietin (TPO), IL-17, and IL-18.

In various embodiments, the support layer is a collagen sheet layer.

In certain embodiments, the support layer is preferably biocompatible, biodegradable, hydrophilic, non-reactive and/or is able to have or has a defined structure.

In certain embodiments, the support collagen sheet layer may be porous or non-porous.

Porous in the sense of the present inventions means that the layer is cell permeable and thus comprises holes through which cells can migrate. In certain embodiments, the support layer has pores with a diameter of 1 μm-2 mm.

On the other hand, non-porous layers do not comprise pores through which cells can migrate. In certain embodiments, the non-porous layers comprise pores through which molecules, but not cells can migrate. The molecules that can penetrate the layer may be only small molecules, such as water or nutrients, such as glucose, or, alternatively, can also be bigger molecules, such as proteins. In other embodiments, the non-porous layers are completely impermeable. In certain embodiments, the support collagen sheet layer is cell porous.

In addition, in various embodiments the support layer is coated or impregnated with an agent or agents to enhance ligament or tendon repair such as hyaluronic acid, angiogenic factors, growth factors, anti-inflammatory compounds, cytokines, and/or collagenase inhibitors. Such agents can immediately diffuse into the body directly to the repair site and/or be released over time or stay resident at the support layer. For the latter effect, the agents can be formulated in controlled release formulations, such as sustained release formulations or delayed release formulations.

In various embodiments, the support layer comprises pericard membrane or split skin.

The pericard membrane may be selected from the group including, but not limited to dog, cat, horse, cow, pig, monkey, ape, chimpanzee, sheep or human pericard membrane.

The split skin may be selected from the group including, but not limited to dog, cat, horse, cow, pig, monkey, ape, chimpanzee, sheep or human split skin.

In various embodiments, the support layer comprises porcine pericard membrane or porcine split skin. In some embodiments, the support layer comprises dried porcine split skin.

The pores in the collagenous support layer may be of natural origin or may be the result of a process carried out after the preparation of the collagen layer. For example, pores may be introduced into the support layer by stamping, punching, die cutting and/or blanking.

In one embodiment, the support layer comprises a pericard membrane, which is originally non-porous or essentially poreless, and which is subjected to a process for introducing pores into the membrane. This process leads to the provision of a cell porous collagenous layer made of pericard membrane. For example, pores may be introduced into the pericard membrane by stamping, punching, die cutting and/or blanking. In certain embodiments, the support layer comprises cell porous pericard membrane which is selected from the group including, but not limited to dog, cat, horse, cow, pig, monkey, ape, chimpanzee, sheep or human cell porous pericard membrane. In a certain embodiment, the support layer comprises cell porous porcine pericard membrane.

In various embodiments, the support layer comprises a dried split skin layer, wherein the split skin may be selected from dog, cat, horse, cow, pig, monkey, ape, chimpanzee, sheep or human origin. In one embodiment, the support layer comprises a dried porcine split skin layer (Xenoderm).

Thus, as shown in FIGS. 1A and 1B, the repair patch employed in the present invention may be an implantable ligament or tendon repair patch 10 comprising two layers that is bio-compatible and physiologically absorbable, and that functions in situ to promote the regeneration of ligament or tendon tissue in ligament or tendon injury. The present ligament or tendon repair patch 10 is a flexible laminate 12 that can be implanted at an injury site and act to promote the regeneration of ligament or tendon tissue. The objective of the ligament or tendon repair patch 10 is to stimulate repair of ligament or tendon tissue in-situ, e.g. following arthroscopic or open surgical application of the ligament or tendon repair patch 10 in patients with ligament and/or tendon injuries. The patch may consist of a support layer (porous in 1A, non-porous in 1B) and a matrix layer 30 comprising collagen fibers 36, hyaluronic acid fibers 40, Diacerein 46a, and Rhein 46b.

In certain embodiments, the ligament or tendon repair patch 10 is biodegradable through the interaction of its constituents with collagenase and other proteases and will be reabsorbed and disappear over time. Under these circumstances, the laminate 12 of the ligament or tendon repair patch 10 is constructed completely of materials that are both bio-compatible and physiologically absorbable, so that the ligament or tendon repair patch can be implanted indwelling in a patient and disappear from the implantation site over time.

Generally, a matrix layer may be made of natural or synthetic material. Synthetic matrices are made predominantly of polymeric materials. Synthetic matrices offer the advantage of a range of carefully defined chemical compositions and structural arrangements. Some synthetic matrices are not degradable. While the non-degradable matrices may aid in repair, non-degradable matrices are not replaced by remodeling and therefore often cannot be used to fully regenerate ligaments or tendons. It is also undesirable to leave foreign materials permanently in a joint due to the problems associated with the generation of wear particles, thus degradable materials are preferred. Degradable synthetic matrices can be engineered to control the rate of degradation.

In certain embodiments, the matrix layer comprises collagen and hyaluronic acid and is prepared such that it is preferably compressible and/or resilient and has some resistance to degradation, e.g. by synovial fluid and catabolic enzymes of the inflammatory process. Synovial fluid as part of normal joint activity naturally prevents clot formation.

A matrix layer may be a solid material such that its shape is maintained, or a semi-solid material capable of altering its shape and/or size. A matrix layer may be made as expandable material allowing it to contract or expand as required. In certain embodiments, the matrix layer is capable of absorbing plasma, blood, other body fluids, cells, proteins, polymers, liquid, hydrogel, or other material the matrix layer either comes into contact with or is added to the matrix layer.

In further embodiments, the matrix layer is a porous collagenous layer. In certain embodiments, the pores of the collagenous matrix layer are cell porous.

In certain embodiments, the collagenous matrix layer is made of collagen fibers or highly crosslinked collagen.

In certain embodiments, the matrix layer comprises a collagen fiber matrix.

The collagen of the matrix layer may be selected from animal or vegetal origin.

In certain embodiments, the collagen of the matrix is selected from the group including, but not limited to collagen of dog, cat, horse, cow, sheep, pig, monkey, ape, chimpanzee, sheep, human or plant origin.

In various embodiments, the collagen of the matrix layer comprises collagen of porcine, equine, bovine or plant origin.

In certain embodiments, the collagenous matrix layer comprises a collagenous biologically acceptable sol-gel, gel, fiber matrix, sponge, foamed collagen, scaffold, honeycomb, hydrogel, or polymer mesh.

In various embodiments, the matrix is a simple sol-gel solution, a colloidal suspension which, under certain conditions, transitions from a liquid (sol) to a solid material (gel). The sol is a suspension of aqueous collagen that is transitioned, by heat treatment, into a gel.

In various embodiments, the matrix layer comprises collagen which may be prepared from type I, II, III, IV, V, VI, VII, VIII, IX, and/or type X collagen. In certain embodiments, the matrix layer is made of type I collagen, type II collagen, type IV collagen, cell-contracted collagen containing proteoglycans, glycosaminoglycans or glycoproteins, and/or gelatin. In various embodiments, the matrix layer further comprises agarose, polymers of aromatic organic acids, fibronectin, laminin, bioactive growth factors, anti-inflammatory compounds, cytokines, elastin, fibrin, natural and/or synthetic polymeric fibers made of poly-acids such as polylactic, polyglycolic or polyamino acids, polycaprolactones, polyamino acids, polypeptide gel, copolymers thereof and combinations thereof. In certain embodiments, the matrix comprises a gel solution matrix which may be a polymeric thermo-reversible gelling hydrogel.

In various embodiments, the matrix layer is coated by natural or non-natural polymer(s). The coating comprises a gel, specifically a hydrogel, selected from the group consisting of sodium alginate, hyaluronic acid, crosslinked hyaluronic acid, crosslinked calcium alginate and a calcium alginate crosslinked hyaluronic acid mixture.

Hyaluronic acid, also called hyaluronan or hyaluronate, is a glycosaminoglycan. It is a naturally occurring biopolymer having biological functions from bacteria up to higher animals including humans. In animals, it is one of the chief components of the extracellular matrix. It contributes significantly to cell proliferation and migration, and may also be involved in the progression of some malignant tumors. Hyaluronan is naturally found in many tissues of the body such as skin, cartilage and the vitreous humor. It is therefore well suited to biomedical applications targeting these tissues. The hyaluronan that can be used in the present invention can be of any molecular weight, for example from about 100 kDa to several million Da, preferably between 500 kDa and 6000 kDa. In various embodiments, the hyaluronic acid of the matrix layer comprises natural hyaluronic acid. In certain embodiments, the hyaluronic acid of the matrix is selected from the group including, but not being limited to hyaluronic acid of dog, cat, horse, cow, pig, monkey, ape, chimpanzee, sheep, human, vegetal or microbial origin.

In various embodiments, the hyaluronic acid of the matrix layer comprises natural, non-human hyaluronic acid.

In certain embodiments, the natural hyaluronic acid of the matrix layer comprises natural, non-human hyaluronic acid from a bacterial fermentation source.

The bacterial production of hyaluronic acid (HA) involving a *Streptococcus zooepidemicus* strain was first described in 1989, giving rise to the first commercialization of fermented HA.

Ultra-pure sodium hyaluronate, marketed as HyaCare by Novozymes is produced by fermentation of a novel and non-pathogenic strain, *Bacillus subtilis*, from which products are Generally Regarded As Safe (GRAS).

In certain embodiments, the hyaluronic acid may be of *Streptococcus zooepidemicus* or *Bacillus subtilis* source.

In various embodiments, the matrix comprises hyaluronic acid in form of fibers, powder, solution, gel or cream suspension.

In certain embodiments, the collagen matrix is dipped into a hyaluronic acid solution or gel. Thereby, the matrix is dispersed by the hyaluronic acid.

In various embodiments, the matrix layer comprises collagen copolymerized with hyaluronic acid.

The repair patch employed in the method of the present invention may comprise a certain weight range ratio of collagen to HA, which is advantageous in ligament or tendon repair. In certain embodiments, the weight range ratio of collagen to HA is about 0.1:99.9 to about 50:50 if the HA has a molecular weight of between 0.5 to 6 million Dalton.

In certain embodiments, the matrix layer is a cell porous collagenous composite pad interspersed with collagen fibers and natural hyaluronic acid dispersed into the vacant spaces of the collagen fibers.

In some embodiments, the matrix layer comprises collagen, hyaluronic acid and poly lactic acid, e.g., poly-L-lactic acid. For example, the matrix layer may be a cell porous collagenous composite pad interspersed with collagen fibers and natural hyaluronic acid and poly lactic acid, e.g., poly-L-lactic acid, dispersed into the vacant spaces of the collagen fibers.

The matrix layer may further comprise protein, lyophilized material, or any other suitable material. In this context, a protein can be synthetic, bioabsorbable or a naturally occurring protein. In various embodiments, the matrix layer includes proteins selected from the group of extracellular matrix proteins. The group of extracellular matrix proteins includes, but is not limited to fibrin, elastin, fibronectin, and laminin.

Lyophilized material is material that is capable of swelling when liquid, gel or other fluid is added or comes into contact with it.

In various embodiments, the matrix layer further comprises glycosaminoglycan (GAG), hyaluronan compositions, and various synthetic compositions.

Collagen-glycosaminoglycan (CG) copolymers have been used successfully in the regeneration of dermis and peripheral nerve. Porous natural polymers, fabricated as sponge-like and fibrous scaffolds, have been investigated as implants to facilitate regeneration of selected musculoskeletal tissues including ligaments and tendons. A scaffold, such as a sponge scaffold, may also be made from tendon (xenograft, allograft, autograft) or ligament or skin or other connective tissue which could be in the native state or processed to facilitate cell ingrowth or other biologic features.

In various embodiments, the matrix layer comprises Collagen-glycosaminoglycan (CG) copolymers.

Glycosaminoglycans (GAGs) or mucopolysaccharides are polysaccharides made up of residues of hexoamines glycosidically bound and alternating in a more-or-less regular manner with either hexouronic acid or hexose moieties. GAGs are of animal origin and have a tissue specific distribution (see, e.g. Dodgson et al., in Carbohydrate Metabolism and its Disorders, Dickens et al., eds., Vol. 1, Academic Press (1968)). Reaction with the GAGs also provides collagen with another valuable property, i.e., inability to provoke an immune reaction (foreign body reaction) from an animal host.

In certain embodiments, the matrix comprises GAGs which include, but are not limited to those containing sulfate groups, such as hyaluronic acid, heparin, heparin sulfate, chondroitin 6-sulfate, chondroitin 4-sulfate, dermatan sulfate, and keratin sulfate.

Other GAGs also may be suitable for forming the matrix described herein, and those skilled in the art will either know or be able to ascertain other suitable GAGs using no more than routine experimentation. For a more detailed description of mucopolysaccharides, see Aspinall, Polysaccharides, Pergamon Press, Oxford (1970).

In certain embodiments, the matrix comprises at least one or more collagen-GAG copolymers, which include, but are not limited to hyaluronic acid, heparin, heparin sulfate, chondroitin 6-sulfate, chondroitin 4-sulfate, dermatan sulfate, and keratin sulfate.

In certain aspects of the invention, the matrix layer comprises a sponge or sponge-like structure.

The material establishing the sponge scaffold may be hydrophilic. A sponge scaffold is capable of compression and expansion as desired. For example, a sponge scaffold may be compressed prior to or during implantation into a repair site. A compressed sponge scaffold allows for the sponge scaffold to expand within the repair site. A sponge may be lyophilized and/or compressed when placed in the repair site and expanded once in place. The expansion of a sponge scaffold may occur after contact with blood or other fluid in the repair site or added to the repair site. A sponge scaffold may be porous. A sponge scaffold may be saturated or coated with a liquid, gel, or hydrogel repair material prior to implantation into a repair site. Coating or saturation of a sponge scaffold may ease implantation into a relatively undefined defect area as well as help to fill a particularly large defect area. In a preferred embodiment, a sponge scaffold is treated with a hydrogel. Examples of scaffolds and repair materials useful according to the invention are found in U.S. Pat. No. 6,964,685 and US Patent Application Nos. 2004/0059416 and 2005/0261736, the entire contents of each are herein incorporated by reference. All matrix coatings disclosed in the present application documents are herewith explicitly disclosed as suitable coatings for sponge scaffold matrices.

In various embodiments, collagen establishes a sponge scaffold.

In various embodiments, the matrix layer further comprises one or more from the following polymers: natural or synthetic polymers, resorbable or non-resorbable polymers.

Examples of resorbable polymers include, but are not limited to, poly(alpha-hydroxy acids), polylactide-co-glycolide (PLGA), polylactide (PLA), polyglycolide (PG), polyethylene glycol (PEG) conjugates of poly(alpha-hydroxy acids), polyorthoesters, polyaspirins, polyphosphazenes, elastin, silk, cellulose starch, chitosans, gelatin, alginates, cyclodextrin, polydextrose, dextrans, vinylpyrrolidone, polyvinyl alcohol (PVA), PVA-g-PLGA, polyethyleneglycol-terephtalate and polybuthylene-terephtalate (PEGT-PBT) copolymer (polyactive), methacrylates, poly(N-isopropylacrylamide), polyethylene oxides (also known as polyoxyethylene or PEO), poly-propylene oxide (also known as polyoxypropylene or PPO), poly (aspartic acid) (PAA), PEO-PPO-PEO (Pluronics®, BASF), PEO-PPO-PAA copolymers, PLGA-PEO-PLGA, polyphosphoesters, polyanhydrides, polyester-anhydrides, polyamino acids, polyurethane-esters, polyphosphazines, polycaprolactones, polytrimethylene carbonates, polydioxanones, polyamide-esters, polyketals, polyacetals, glycosaminoglycans, chondroitin sulfate, hyaluronic acid esters, polyethylene-vinyl acetates, silicones, polyurethanes, polypropylene fumarates, polydesaminotyrosine carbonates, polydesaminotyrosine arylates, polydesaminotyrosine ester carbonates, polydesaminotyrosine ester arylates, polyorthocarbonates, polycarbonates, or copolymers or physical blends thereof or combinations thereof.

The term "chitosans" and "chitosan and its derivatives" relates to the group of compounds including, but not limited to chitosan, chitosan hydrochloride, carboxymethyl chitosan, chitosan lactate, chitosan acetate, chitosan glutamate, chitosan succinate, N-(2-hydroxy)propyl-3-trimethyl ammonium chitosan chloride, N-trimethylene chitosan chloride, and pharmaceutically acceptable salts thereof.

Non-resorbable polymers can include, but are not limited to, polyethylene, delrin, silicone, polyurethane, copolymers of silicone and polyurethane, polyolefins such as polyisobutylene and polyisoprene, acrylamides such as polyacrylic acid and poly(acrylonitrile-acrylic acid), neoprene, nitrile, acrylates such as polyacrylates, poly(-hydroxy ethyl methacrylate), methyl methacrylate, 2-hydroxyethyl methacrylate, and copolymers of acrylates with N-vinyl pyrrolidone, N-vinyl lactams, acrylamide, polyurethanes and polyacrylonitrile, glucomannan gel, alkyl celluloses, hydroxyalkyl methyl celluloses, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. The vulcanized rubber described herein may be produced, for example, by a vulcanization process utilizing a copolymer produced as described, for example, in U.S. Pat. No. 5,245,098 to Summers et al. from 1-hexene and 5-methyl-1,4-hexadiene.

Other suitable non-resorbable material include, but are not limited to, lightly or highly cross-linked biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, sulfonated polymers, vinyl ether monomers or polymers, alginate, polyvinyl amines, polyvinyl pyridine, and polyvinyl imidazole.

In certain embodiments, the above polymers are cross-linked with the collagen and/or hyaluronic acid of the matrix layer.

The skilled person is well aware of that depending on the amount of crosslinking within the bioresorbable polymers, the degradation time of the polymer can be reduced, thus allowing the control of the rate of matrix degradation.

In various embodiments, the matrix layer further comprises one or more compounds selected from analgesics, anti-inflammatory agents, antibiotics, and agents promoting ligament or tendon regeneration.

These compounds are in the sense of the present invention selected from the group comprising, but not limited to small molecules, proteins, RNA, DNA, PNA.

Thus, the matrix may incorporate therapeutic proteins including, but not limited to, hormones, cytokines, growth factors, anti-inflammatory compounds, clotting factors, anti-protease proteins, e.g., alpha-1-antitrypsin, angiogenic proteins, e.g. vascular endothelial growth factor, fibroblast growth factors, antiangiogenic proteins, e.g. endostatin, angiostatin, and other proteins that are present in the blood, bone morphogenetic proteins (BMPs), osteoinductive factor (IFO), fibronectin (FN), endothelial cell growth factor (ECGF), cementum attachment extracts (CAE), ketanserin, human growth hormone (HGH), animal growth hormones, epidermal growth factor (EGF), human alpha thrombin, transforming growth factor (TGF-beta), insulin-like growth factor (IGF-I), platelet derived growth factors (PDGF), fibroblast growth factors (FGF, bFGF, etc.), and periodontal ligament chemotactic factor (PDLGF), somatotropine, for therapeutic purposes, and extracellular matrix proteins, including but not limited to fibrin, elastin, fibronectin, laminin.

Anti-inflammatory compounds are chemicals that reduce or prevent an inflammatory response at a given site. The group of anti-inflammatory compounds includes, but is not limited to Diacerein and Rhein.

The Diacerein 46a and the Rhein 46b (see FIGS. 1 and 2) inhibit the production and activity of inflammatory cytokines such as interleukin-1 (IL-1), IL-6, nitric oxide (NO), tumour necrosis factor-alpha (TNF-α), ADAMTS (A Disintegrin And Metalloproteinase with Thrombospondin Motifs), free radicals and matrix metalloproteinases all of which are involved in inflammation and ligament and tendon destruction. Diacerein 46a and Rhein 46b also stimulate the production of growth factors such as TGF-β which in turn stimulates expression of ligament and tendon components such as hyaluronic acid, proteoglycans, aggrecans and collagenase II, all of which are important components of ligament and tendon tissue. The growth hormone will also stimulate the growth of ligament and tendon tissue.

In certain embodiments, the matrix comprises small molecules selected from the group including, but not limited to Aspirin, Paracetamol, Diclofenac, Ibuprofen and water.

In certain embodiments, the agents promoting ligament or tendon regeneration are selected from the group consisting of: growth factors, Diacerein, Rhein, chitosans, platelet rich plasma (PRP), and poly-lactic acid. Thus, in some embodiments, the matrix layer comprises or consists of collagen, hyaluronic acid, and chitosan or chitosans.

In various embodiments, the Diacerein and/or Rhein amounts in the patch are in the range of about 300 ng to 5 mg. In certain embodiments, the Diacerein and/or Rhein amounts in the patch are in the range of about 300 ng to 75 μg. In some embodiments, the Diacerein and/or Rhein amounts in the matrix layer are in the range selected from the group consisting of 300 ng to 5 mg, 300 ng to 1 mg, 300 ng to 750 μg, 300 ng to 500 μg, 300 ng to 250 μg, 300 ng to 100 μg, 300 ng to 75 μg, 300 ng to 50 μg, 300 ng to 25 μg, 300 ng to 10 μg, 300 ng to 5 μg, 300 ng to 2.5 μg, and 300 ng to 1 μg.

The Diacerein and/or Rhein may be added to the matrix in a powder form, as solution or as HA gel or cream containing Diacerein and/or Rhein.

Anionic polymers may also be useful to inhibit fibrosis, scars, or adhesions. In certain embodiments the matrix further comprises anionic polymers. The group of anionic polymers includes, but is not limited to dextran sulfate, pentosan, chitosans.

The matrix layer may further comprise blood. The term blood includes full blood, blood plasma, blood serum and components isolated from blood, and may be of autologous or heterologous origin. In certain embodiments, the repair patch is first soaked with blood such that the matrix layer comprises blood and then applied to the injured ligament or tendon. In alternative embodiments, the repair patch is first applied to the injured ligament or tendon and then blood is added to the attached patch or received from the injured site such that the matrix layer comprises blood. In particular, the matrix layer of the repair patch may comprise blood serum, which is applied to the patch before or after application of the patch to the injured ligament or tendon.

Blood plasma in the sense of the present invention includes the part of the blood which is remaining after separation of the cellular components of blood. This fraction corresponds to about 55% of the blood volume. Blood plasma comprises water, proteins, carbohydrates, electrolytes, fats and lipids. The group of blood plasma proteins comprises immunoglobulins, albumins, hormones and coagulation factors. The group of coagulation factors comprises Fibrinogen (Factor I), Fibrin (Factor Ia), Prothrombin (Factor II), Thrombin (Factor IIa), Thromboplastin (also named Tissue Factor, TF or Factor III), Proaccelerin (Factor V), Proconvertin (Factor VII), Antihemophilic Globulin A (Factor VIII), Antihemophilic globulin B (also named Factor IX or Christmas-Factor), Stuart-Prower-Factor (Factor X), Plasma Thromboplasmin Antecedent (also named PTA, Factor XI or Rosenthal-Factor), Hageman-Factor (Factor XII) and Fibrin stabilizing Factor (Factor XIII). The group of coagulation factors comprises the inactive and activated variants of the coagulation factors. The person skilled in the art labels the activated coagulation factors by adding an "a", for example Ia, IIa, IIIa, VIIa, VIIIa, IXa, Xa, XIa, XIIa, and XIIIa.

Blood serum is the liquid fraction of blood which remains after blood coagulation and separation of the cellular blood components. Essentially, the composition of blood serum corresponds to the composition of blood plasma less the spent coagulation factors.

In various embodiments, the patch further comprises a third layer, which is disposed on the matrix layer such that the matrix layer is sandwiched between the support layer and the third layer.

In certain embodiments, the third layer includes, but is not limited to poly(alpha-hydroxy acids), polylactide-co-glycolide (PLGA), polylactide (PLA), polyglycolide (PG), polyethylene glycol (PEG) conjugates of poly(alpha-hydroxy acids), polyorthoesters, polyaspirins, polyphosphazenes, collagen, elastin, silk, cellulose starch, chitosans, gelatin, alginates, fibronectin, laminin, elastin, fibrin or combinations thereof.

In various embodiments, the third layer comprises a collagen sheet layer.

The origin of the collagen of the collagen sheet layer may be selected from the group including, but not limited to dog, cat, horse, cow, pig, monkey, ape, chimpanzee, sheep or human.

In various embodiments, the third layer comprises pericard membrane or split skin, e.g., dried porcine split skin.

The pericard membrane may be selected from the group including, but not limited to dog, cat, horse, cow, pig, monkey, ape, chimpanzee, sheep or human pericard membrane.

The split skin may be selected from the group including, but not limited to dog, cat, horse, cow, pig, monkey, ape, chimpanzee, sheep or human split skin.

In various embodiments, the third layer comprises porcine, bovine, or equine pericard membrane or porcine split skin.

The collagenous third layer may be cell porous or non-porous.

In some embodiments, the collagenous third layer is cell porous.

If the collagenous third layer comprises pores, the pores in the collagenous third layer may be of natural origin or may be the result of a process carried out after the preparation of the collagen layer.

In one embodiment, the third layer comprises a pericard membrane, which is essentially poreless, and which is subjected to a process for introducing pores into the membrane. This process leads to the provision of a cell porous collagenous layer made of pericard membrane. For example, pores may be introduced into the pericard membrane by stamping, punching, die cutting and/or blanking. In certain embodiments, the third layer comprises cell porous pericard membrane which is selected from the group including, but not limited to dog, cat, horse, cow, pig, monkey, ape, chimpanzee, sheep or human cell porous pericard membrane. In a certain embodiment, the third layer comprises cell porous porcine pericard membrane.

In various embodiments, the third layer comprises a dried split skin layer, wherein the split skin may be selected from dog, cat, horse, cow, pig, monkey, ape, chimpanzee, sheep or human origin. In one embodiment, the third layer comprises a dried porcine split skin layer (Xenoderm)

In certain embodiments, the support layer and the third layer are identical in that they are made of the same material. This means that in various embodiments, the third layer is made of the same materials as described above for the support layer.

In various embodiments, the patch comprises a support layer and a matrix layer. In various further embodiments the patch comprises a support layer, a matrix layer and a third layer.

In alternative modes, the patch includes the support and matrix layers, wherein the support layer is made of pericard membrane, and the membrane is non-porous. In a certain embodiment thereof, the pericard membrane is porcine pericard membrane.

In alternative embodiments, the patch includes the support and matrix layers, wherein the support layer is made of pericard membrane, wherein the membrane is cell porous. In a certain embodiment thereof, the pericard membrane is porcine pericard membrane.

In certain embodiments, the patch comprises a support, a matrix, and a third layer, wherein the support and the third layer are non-porous pericard membranes. In a certain embodiment thereof, the non-porous pericard membranes are non-porous porcine pericard membranes.

In certain embodiments, the patch comprises a support, a matrix, and a third layer, wherein the support and the third layer are cell porous pericard membranes. In a certain embodiment thereof, the cell porous pericard membranes are cell porous porcine pericard membrane.

In alternative modes, the patch comprises a support, a matrix, and a third layer, wherein the support and the third layer are pericard membranes, wherein either the support or the third layer is non-porous and the other layer is cell porous. In a certain embodiment thereof, the pericard membranes are porcine pericard membranes. In certain embodiments thereof, the patch is applied such that the non-porous layer faces the ligament or tendon injury site, wherein in other embodiments, the patch is applied to the injury site such that the cell porous layer faces the injured site.

Under certain circumstances it may be further advantageous to apply a patch comprising a non-porous support and/or third layer to the injured ligament or tendon. Thereby, growth factors secreted from cells resident beneath or next to the injured site are entrapped and locally concentrated thereby leading to an enhanced growth of cells at the injured site and a more rapid ligament or tendon repair. Furthermore, compounds and cells adverse to the ligament or tendon repair are excluded from the injury site.

Also, patches comprising a support layer and a matrix layer, wherein the support layer is non-porous and the patch is applied to the injured ligament or tendon with the matrix facing the injury, are advantageous, as growth factors supplied by autologous centrifuged serum fractions, PRP or subchondral blood clot will, in conjunction with subchondral, synovial or fat MSC's seeded in the collagen support or matrix layer, enhance the repair process at the ligament and/or tendon injury site or at the autologous, allo- or xenograft surface. Furthermore, exogenous compounds, e.g. growth factors and anti-inflammatory compounds, which have been added to the matrix prior to the application of the patch to the injury, are released towards the injured ligament or tendon only. Thereby, at the injured site the concentration of exogenous compounds is increased compared to conditions wherein the compounds are allowed to diffuse omni-directional. This enhances the benefits from the exogenous compounds.

If the patch comprises a support and a matrix layer, the layers of the patch can be laminated together using heat, or chemicals, or other suitable laminating techniques. In certain embodiments, first one layer is formed and then the second on top of it. For example, first the matrix layer is formed then the support layer is formed on top of it. Alternatively, first the support layer is formed then the matrix layer on top of the support layer.

If the patch comprises a support, a matrix layer and a third layer, the layers of the patch can be laminated together using heat, or chemicals, or other suitable laminating techniques. In certain embodiments, first one layer is formed and then the second on top of it and the third layer is formed on the composite of the first and the second layer. For example, first the matrix layer is formed then the support layer is formed on top of the matrix layer. In a third step, the third layer is formed on the matrix layer, sandwiching the matrix layer with the support layer. Alternatively, first the support/third layer is formed then the matrix layer on top of the support/third layer and then the third/support layer on top of the matrix layer, on the opposite site of the support/third layer. In further embodiments, the three layers are layered over each other and the patch is laminated in a single step.

The implantable laminate ligament or tendon repair patch is a surgical device that is bio-compatible. In certain embodiments, the patch is physiologically absorbable. In various embodiments, the patch is intended for in situ ligament or tendon repair.

In some embodiments, the patch is adapted in that it allows in certain embodiments the migration of cells from the injury site to pass into the matrix layer. The matrix layer is a collagenous layer and may be a sink for the diffusion of autologous stem cells and other blood components at the injury site. The matrix layer may include chemical components which promote ligament and/or tendon repair in the presence of autologous stem cells of subchondral, synovial, fat, or hematopoietic origin. Thus, in some embodiments the patch is positioned on the injury site with the matrix layer facing the injured site. Also optionally, the matrix layer may be occluded by the support and/or third layer, such that cells cannot pass through to the matrix, but allowing other small compounds, like water, gas and small molecules to pass through. Thereby, the present invention provides an in situ healing/tissue growth promoting method to repair ligament or tendon injuries.

Figure 4:
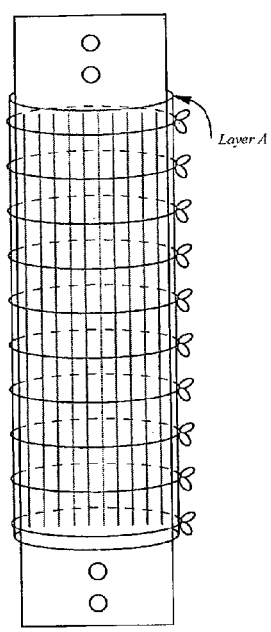
FIG. 4 shows a possible application procedure of the patch of the present invention (layer A) to a graft, wherein the patch is fixed to the graft using an autologous growth factor enhanced glue injected between the graft and the patch and circular threads. If the patch consists of a support and a matrix layer, it may be applied with the matrix or support layer facing the injury site, wherein in some embodiments it is preferred if the matrix layer faces the injury site. In further embodiments, if the patch comprises a support, matrix, and a third layer, the patch may be applied with the support or third layer facing the injury site. Exemplary patches are detailed in FIGS. 1A, 1B, 2A-2E and 3.
Figure 5:
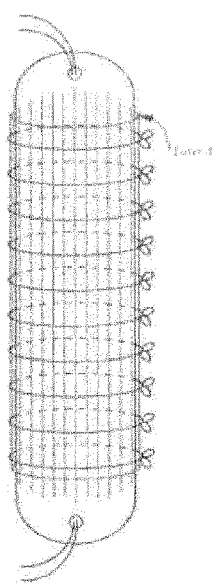
FIG. 5 shows an additional schematic drawing of a ligament or tendon graft without bony attachments. The patch (layer A) of the present invention, e.g., a patch as detailed in FIGS. 1A, 1B, 2A-2E and 3, is cut to a length and width approximately corresponding to the size of the graft. The patch is fixed to the graft using a autologous growth-factor enhanced glue injected between the graft and the patch and circular threads.
Figure 6A:
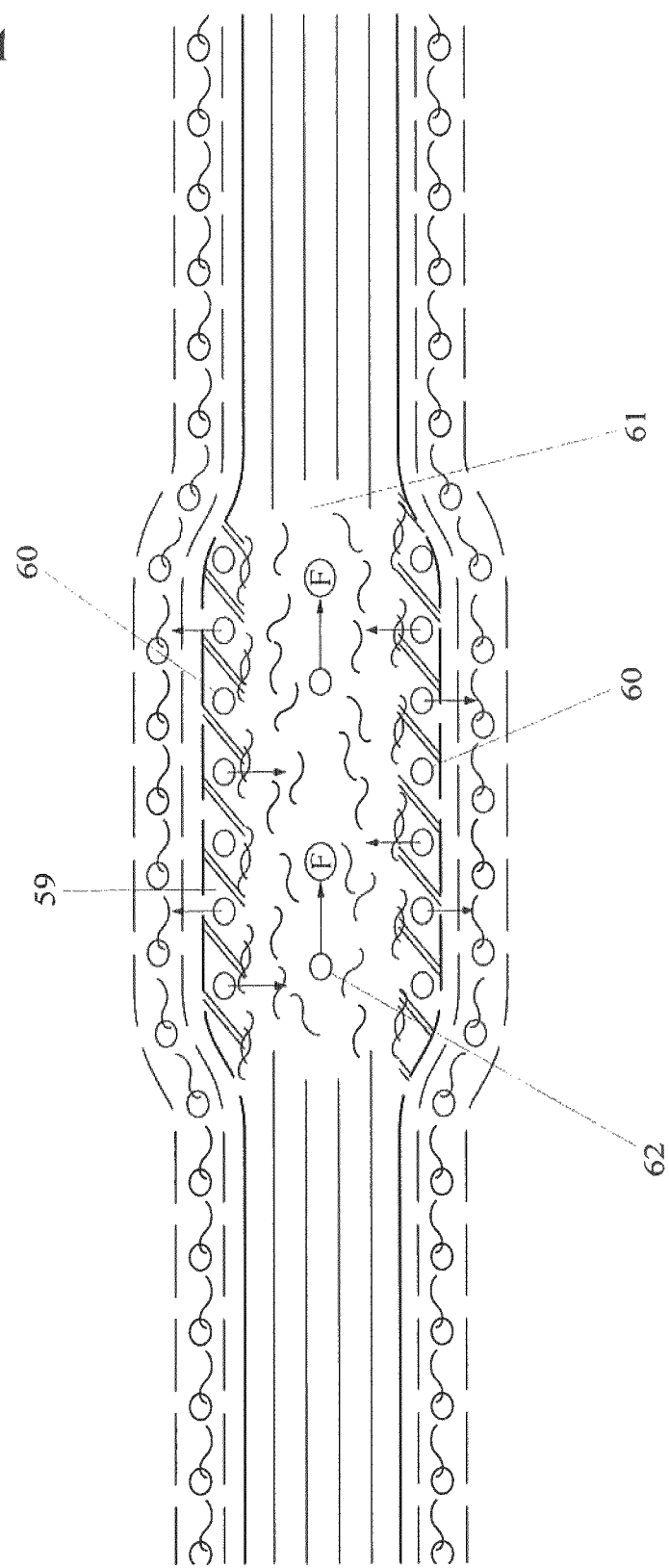
FIG. 6a: tendon/ligament repair patch side-view.
Figure 6B:
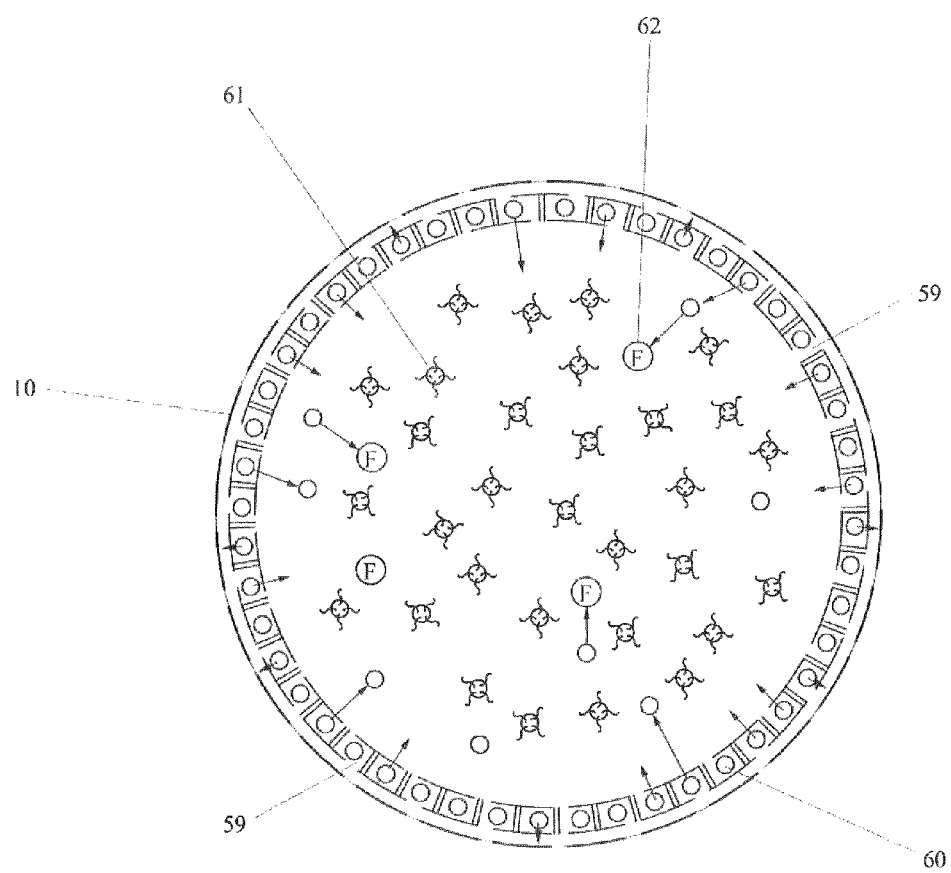
FIG. 6b: tendon/ligament repair process cross-section.

In certain embodiments, the ligament or tendon repair patch laminate 12 has a third layer, which is optionally occlusive or porous, layer 16, and a porous support layer 22 (see FIGS. 2A to 2C and 3). In another preferred embodiment, the ligament or tendon repair patch laminate 12 includes only two layers, a support layer 22 and a matrix layer 30 (see FIGS. 2D and 2E). In various embodiments, the support layer is intended to face the surface of the ligament or tendon at the injury site. In various embodiments, the third layer is intended to face the surface of the ligament or tendon at the injury site. In other embodiments, the matrix layer of a two layer patch faces the ligament or tendon injury site (see also FIGS. 4 and 5). Both, the third layer 16 and/or the support layer 22 of a three layer repair patch may be made of sheet collagen (see Angele et al., U.S. Pat. No. 6,737,072 the content of which is incorporated herein by reference). An example of a satisfactory commercially available source of sheet collagen is: XENODERM™, mbp bH, Germany. In certain embodiments, the matrix layer 30 provides a collagenous substrate in which to entrap mesenchymal stem-cells or ligament or tendon stem cells, and a cell growth support medium on which they will grow and differentiate in presence of the other natural components of the matrix layer 30.

In various embodiments, the matrix layer 30 is a porous collagenous composite pad, interspersed with non-human collagen fibers 36 and natural hyaluronic acid fibers 40. The natural HA can be provided in the matrix 30 in form of natural HA fibers 40 as shown in FIG. 2A, or as HA powder 40a in a gel or cream suspension 42 dispersed into the vacant spaces of the collagen fibers 36 as in FIG. 2B.

In certain embodiments, the matrix layer 30 (see FIG. 2B) also includes one or more tissue growth hormones and/or anti-inflammatory compounds 46. In certain embodiments, the anti-inflammatory compounds are Diacerein 46a and Rhein 46b. In the embodiment illustrated in FIG. 2B, the suspension 42 also contains Rhein 46b and/or Diacerein 46a. In various embodiments, the matrix layer 30 further includes chitosan compositions and/or poly-lactic acid compositions.

The repair patch is configured, in various embodiments of the method of the present invention, such that autologous mesenchymal stem cells 60 derived from a source external to the repair patch 10 diffuse into the patch 10 through the porous support layer 22 and into the matrix layer 30 where they are supported by the fibrous components (collagen fibers 36 and/or HA fibers 40a) of the matrix 30 (for example FIGS. 2A-2E, 3, 6a and 6b). In various embodiments, the matrix fibers 40 & 40a may provide a support medium for the stem cells to grow and differentiate into ligament or tendon cells. The exogenous factors 46, such as Diacerein down regulate inflammatory parameters (e.g., cytokines: IL-1, TNF-alpha, and free radicals) which contribute to inflammation. In certain embodiments, one or more growth hormones are present in the matrix layer. Those one or more growth hormones may stimulate the production of ligament and/or tendon tissue.

In various embodiments, the repair patch may comprise a support, matrix, and third layer, wherein the support layer comprises a perforated split skin layer, e.g., a porcine split skin layer (Xenoderm), and the third layer comprises a non-perforated split skin layer, e.g., a porcine split skin layer (Xenoderm). Alternatively, both, the support and the third layer, comprise a perforated split skin layer, e.g., a porcine split skin layer (Xenoderm). In certain embodiments, the support and the third layer consist of a split skin layer. In some embodiments, the matrix layer may comprise collagen, hyaluronic acid and poly lactic acid, e.g., poly-L-lactic acid. For example, the matrix layer may be a cell porous collagenous composite pad interspersed with collagen fibers and natural hyaluronic acid and poly lactic acid, e.g., poly-L-lactic acid, dispersed into the vacant spaces of the collagen fibers. In some embodiments, the matrix layer may comprise further compounds as disclosed herein, e.g., growth factors, chitosans, Rhein, and Diacerein.

Generally, the repair patch of the present invention enhances tendon and ligament repair, strengthens, and favors integration of autologous ligament and tendon grafts. In certain embodiments, the matrix layer is used as a support structure for exogenously adding, adhering, incorporating, embedding or seeding cells, such as fibroblasts, tenocytes, their progenitors, mesenchymal cells, ligament or tendon cells, stem cells of different origins to the site of treatment. These cells are added, according to the invention, to increase or provide stimulation to enhance the repair process at the injured ligament or tendon site or at the ligament and/or tendon graft site. Suitable cells to be used in this invention are the cells that are either autologous or heterologous cells, such as allogenic or xenogenic cells, cell lines and/or procaryotic cells. Typically, the cells added exogenously to the matrix layer or to a collagenous scaffold are obtained commercially or isolated from the ligaments or tendons cultured in vitro using methods know in the art.

The method, in one embodiment, comprises the in vitro and ex vivo addition of progenitor cells, mature fibroblasts, ligament or tendon cells or other cells to the device of the invention by adhering, incorporating, embedding or seeding the cells into the collagenous scaffold matrix layer or to the support/third layer. The cultured cells are added to the matrix layer as such or are adhered to the support layer and/or third layer before, during or even after the surgery. The exogenously added cells may induce production or produce proteins and matrix components consistent with neo-ligaments or neo-tendons or induce migration of the native cells from the uninjured ligament or tendon to the site of injury.

In various embodiments, the patch has a thickness of between 0.1-10 mm, 0.5-2 mm, 0.5-1 mm or 0.75-1.25 mm.

If the patch includes laminated support and matrix layers, the patch may be applied to the injured ligament with the matrix layer facing the ligament. In an alternative mode, the patch may be applied to the injured ligament with the support layer facing the ligament. Herewith, the same application modes of the patch are disclosed for application to injured tendons.

If the patch includes laminated support, matrix and third layers, the patch may be applied to the injured ligament with the third layer facing the ligament. In an alternative mode, the patch may be applied to the injured ligament with the support layer facing the ligament. Herewith, the same application modes of the patch are disclosed for application to injured tendons.

In certain embodiments, the patch comprises a cell porous collagenous support layer and a matrix layer and the patch may be applied to the injured ligament with the support layer facing the ligament. In alternative embodiments, the patch includes a cell porous collagenous support layer and a matrix layer and the patch may be applied to the injured ligament with the matrix layer facing the ligament. In further embodiments, the patch comprises a cell porous collagenous third layer, a cell porous collagenous support layer and a matrix layer and the patch may be applied to the injured ligament with the third layer or support layer facing the ligament. In further embodiments, the patch comprises a cell porous collagenous third layer, a non-porous collagenous support layer and a matrix layer and the patch may be applied to the injured ligament with the third layer or support layer facing the ligament. In further embodiments, the patch comprises a non-porous collagenous third layer, a non-porous collagenous support layer and a matrix layer and the patch may be applied to the injured ligament with the third layer or support layer facing the ligament. These application modes of the patch are similarly suitable for application to injured tendons.

In certain embodiments, the support layer is coated with Glycosaminoglycans (GAGs) or mucopolysaccharides disclosed herein. In some embodiments, the support layer is coated with hyaluronic acid as disclosed herein.

In further embodiments, if the patch comprises a third layer, the third layer is coated with Glycosaminoglycans (GAGs) or mucopolysaccharides disclosed herein. In various embodiments, the third layer is coated with hyaluronic acid as disclosed herein.

In certain embodiments, the patch is designed such that the patch is completely bioabsorbable. Hence, once implanted the patch automatically degrades over time. The skilled person is well capable to design the patch such that the patch degrades during ligament or tendon healing or after healing of the ligament or tendon is achieved.

In various embodiments, the patch is not biodegradable and has to be explanted once the ligament or tendon is repaired.

The methods of the present invention are suitable for ligament and/or tendon repair.

In various embodiments, the ligament is selected from the group of ligaments, but not being limited to, connected to lower and upper extremities, head and neck e.g., shoulder, elbow, wrist, hand, hip, knee, foot ankle and spine.

In certain embodiments, the ligament is selected from the group comprising, but not being limited to cricothyroid ligament, periodontal ligament, suspensory ligament of the lens, suspensory ligament of the breast, anterior sacroiliac ligament, posterior sacroiliac ligament, sacrotuberous ligament, sacrospinous ligament, inferior pubic ligament, superior pubic ligament, suspensory ligament of the penis, palmar radiocarpal ligament, dorsal radiocarpal ligament, ulnar collateral ligament, radial collateral ligament, cruciate ligament, anterior cruciate ligament (ACL), lateral collateral ligament (LCL), posterior cruciate ligament (PCL), medial collateral ligament (MCL), and patellar ligament.

In various embodiments, the tendon is selected from the group of tendons, but not being limited to, tendons connected to lower and upper extremities, such as tendons in elbow, hands, knee, foot and ankle, and tendons in the shoulder, hip, and spine, thoracic, and abdominal tendons.

In certain embodiments, the tendon is selected from the group comprising, but not being limited to Achilles tendon, biceps brachii tendon, triceps brachii tendon, long extensor tendon, and peroneal tendon, tibialis ant. and post. tendons, subscapularis tendon, rotator cuff tendons, quadriceps tendon, and patellar tendon. All tendons present in hand and feet could be included. The method of the present invention may be applied to a patient, wherein the patient is afflicted by a disorder affecting a ligament and/or tendon comprising, but not being limited to inflammation, autoimmune disease, infection, stress, strain, rupture, sprain, avulsion, overstretching, or tearing of the ligament and/or tendon.

In certain embodiments, before the repair patch is applied to the injured ligament and/or tendon, the injury site is prepared for receiving the patch.

In certain embodiments, prior or after attachment to the injured ligament or tendon the repair patch is soaked with blood to entrap autologous mesenchymal stem cells (MSCs) in the patch and release growth factors at the injured site. These pluripotential MSCs in the presence of collagen patch will differentiate into fibroblasts and later mature ligament or tendon cells to repair the ligament or tendon injury site or transform the ligament or tendon graft tissue.

After the injury site is prepared, further procedures may be carried out.

In certain embodiments, in order to fix the repair patch to the injured ligament or tendon, the patch may be fixed to the ligament or tendon using surgical suture. In certain embodiments, the patch is fixed to the injured ligament or tendon by suturation and/or tying the patch to the injured ligament/ tendon using suture and/or the addition of glue to the fixation site at the injured ligament or tendon.

The suture may be made of material selected from, but is not limited to dimethylsiloxan, polytetrafluorethylene (PTFE), in particular condensed PTFE (cPTFE) or extended PTFE (ePTFE), polyethylene, polylactic acid, polydioxanone, caprolactone, polyglycolic acid, collagen polyester and acryl-based polymers, for example esters of acrylic acid or methacrylic acid. Particular suitable polymers are for example mixed polymers of polypropylene (PP) and poliglecaprone, polymers of poly-p-dioxanone, polyester, polyvinylidene fluoride (PVDF), polypropylene (PP), in particular condensed PP (cPP), polytetrafluorethylene (PTFE), polymethylmethacrylate (PMMA), polyethyleneterephthalate, polyetherketone (PEK), and polyetheretherketone (PEEK).

The surgical suture may be bio-compatible.

In various embodiments, the repair patch is fixed to the injured ligament or tendon by stitching the patch to the ligament or tendon. Typically, biologically absorbable surgical sutures are used to fix the patch. The surgical sutures may be made of polylactic acid, polydioxanone, and caprolactone, polyglycolic acid and collagen.

In certain embodiments, the repair patch comprises growth factors, anti-inflammatory compounds and/or antibodies which may be of recombinant origin and/or isolated from blood, e.g., autologous blood. Hence, in some embodiments the patch comprises, e.g. TGF-βI and/or one or more growth factors, as described herein.

In certain embodiments, in order to fix the repair patch to the wounded ligament or tendon, the patch may be fixed to the ligament or tendon by glue and/or a weld using surgical suture and/or tying using surgical suture.

The glue and/or the surgical suture may be bio-compatible.

The glue may be selected from the group including, but not limited to gelatine, alginic acid, agarose, starch, fibrin, collagen, laminin, elastin, fibronectin, proteoglycans and/or glycosaminoglycans, e.g. heparan sulfate, chondroitin sulfate and/or keratan sulfate, casein, dextrans, caramellose, pectin, carrageen, and xanthan.

For example, the method of the present system may comprise the preparation and application of the fibrin glue/fibrin glue composition at the injured site. The fibrin glue/fibrin glue composition may mingle with bodily fluids to form bodily fluid fibrin glue composite.

In various embodiments, the method of the present invention may further comprise the step of applying glue, e.g. fibrin glue, to the injured ligament or tendon before and/or after application of the repair patch and/or application of glue, e.g. fibrin glue, to the patch. In certain embodiments, if the patch includes a support layer and a matrix layer, glue, e.g. fibrin glue, may be applied to the support and/or matrix layer before and/or after applying the patch to the injured ligament or tendon. In various embodiments, if the patch includes a support layer, a matrix layer and a third layer, glue, e.g. fibrin glue, may be applied to the support and/or third layer before and/or after applying the patch to the wounded ligament and/or tendon.

In certain embodiments, the glue is fibrin or a fibrin composition. The fibrin composition may comprise fibrin and further components. The further components may be growth factors, anti-inflammatory compounds and/or antibodies. In certain embodiments, the further components, e.g., the growth factors, anti-inflammatory compounds and/or antibodies, are recombinant and/or isolated from blood. Hence, in some embodiments at least one component of the fibrin glue composition is isolated from blood or blood serum, i.e., blood serum retrieved after centrifugation, including several growth factors, like TGF-βI and/or one or more growth factors, as described herein. In various embodiments, the fibrin glue composition comprises at least one autologous growth factor isolated from autologous blood. The fibrin glue composition may then stimulate the differentiation of stem cells at the ligament and/or tendon injury/patch interface.

In certain embodiments, glue, e.g., fibrin glue, is applied to the injury site, followed by the placement of the flexible laminate repair patch to the injury site over the glue at the injury site. The glue, e.g., fibrin glue, also may be freely applied after the repair patch is in place at the injury site to further accomplish adhering the repair patch to the injury site. For example, the glue may be injected to reach the covered injury site. In addition, the patch may be further fixed by surgical suture. Once this step is accomplished, the surgical stages are completed and the ligament/tendon repair patch continues its healing purpose in situ.

In certain embodiments, the patch is applied to the ligament or tendon in situ. Hence, in certain embodiments the patch may be applied to the ligament or tendon in an endoscopic procedure, e.g., an arthroscopic operation.

Alternatively, a ligament/tendon graft is harvested from the patient, then the patch is applied as described above and afterwards the graft is introduced into the surgical prepared site Disclosed herein is also a ligament and/or tendon repair patch as described herein.

Also disclosed herein is a ligament and/or tendon repair patch as described herein for use in the treatment of an injured ligament and/or tendon.

All procedures and devices described herein in connection with ligament repair are herewith also disclosed as procedures relating to tendon repair and vice versa.

EXAMPLES

Example 1: Repair Patch Preparation

A collagen sheet 22 (Xenoderm—porcine type 1 and 3 collagen) was used as the support layer 22. The support layer had mechanical properties to resist shear and pull stress and was resorbable in about 6 weeks. The collagen sheet 22 was put into a form, and then loaded with a collagen-HA suspension to which was added either a solution of Diacerein or Diacerein powder to obtain an amount of 0.3-75 µg in dry-weight in the patch after freeze-drying and sterilization. The result was a double layered collagen-pad with the support layer to be disposed on the injured ligament/tendon site. After manufacturing and before sterilization, the pads were put into a mechanical press to obtain a thickness of 0.5-2 mm. HA-concentration in the dry-frozen end product was in the range of about 0.1% to 2%. The HA is natural HA, that is, non-chemically modified HA, of fermentation origin.

Example 2: Production of a Pericardial Membrane

1. Recovery of Raw Material from Bovine Origin

The bovine heart sacs (pericards) employed as the starting material, after the conventional meat inspection by an official veterinarian in the abattoir, first are separated from attached organ parts and grossly rid of fat and connective tissue. Thereby, sheet-like pieces of approximately 30 cm×15 cm in size and a weight of about one kilogram per piece are obtained. The bovine pericards having been thus prepared are transported in a cold bag loaded with ice from the abattoir to the production site and, depending on the amount of the raw material recovered, intermediately stored there at below −20° C. before they are further processed.

2. Wet-Chemical Processing

The raw pericard pieces first were individually rinsed with purified water, usually soaked with running water, to remove adherent blood and water-soluble protein portions. After soaking, all macroscopically visible residues of fat tissue and basal membranes were removed. This was followed by a treatment with 2% aqueous sodium hydroxide solution at room temperature. The pericard pieces (5,000 grams) remained in the lye bath (37.5 liters) for a total of 16 hours. The removal therefrom was followed by a rinse process taking about 10 minutes in demineralized water, which process was repeated until the pH of the rinse run-off water has been reduced to below 8. This was reached after about 1 hour. If any, basal membranes and fat remainders were still observable, then they were removed in this process stage. The much swollen pericard pieces were then transferred into 37.5 liters of a 10% aqueous saline to adjust the swelling state (partial deswelling) as necessary for the further process steps. A NaCl treatment was carried out at room temperature, which was followed by a rinse process with demineralized water. In order to remove any interfering heavy metal ions and any possible lime inclusions from the pericard material, the material was then subjected to a treatment with 37.5 liters of a EDTA solution adjusted to be weakly alkaline and having the concentration of 0.3 g in 100 ml. Then, the material was rinsed with demineralized water as in the preceding process steps to remove the excess of complexing agent and at the same time to bring the pH value to 8.5. The one-time treatment then following with 37.5 liters of acetate buffer (pH 4.8; composition, per 100 ml: 59 parts by volume of a solution of 0.01 moles of sodium acetate plus 3 $H_2O$ in 100 ml and 41 parts by volume of 0.01 moles of acetic acid in 100 ml) served the purpose of buffering all of the residues, if any, left in the pericard tissue and to prepare a weakly acidic medium for the subsequent bleaching operation. Any excessive buffer substances were removed as described above by rinsing with demineralized water.

3. Oxidative Bleaching

Subsequently to the wet-chemical processing, the pericard pieces were subjected to an oxidative bleaching operation taking one hour in 37.5 liters of a 1.5% hydrogen peroxide solution. The bleaching process was carried out, as well as the preceding process steps were, at room temperature. Thereby, on the one hand, the efficiency of the purification operations is ensured while, on the other hand, a deterioration of the collagenous tissue is avoided.

4. Washing Out

In order to remove any excess of reagent, the material was subsequently rinsed with demineralized water according to the conventional regimen.

5. Degreasing

The rinsed bovine pericard pieces were placed in such an amount of acetone that the bovine pericard tissue was completely covered with acetone. The solvent was three times replaced within 8 hours. The bovine pericard pieces thus dehydrated were then transferred to a Soxhlet apparatus and extracted with acetone for about 8 hours. After the extraction the pericard pieces were air-dried and then re-hydrated in a transportation vessel with demineralized water.

6. Lyophilization

Drying was effected in an automatically controlled freeze dryer. Freeze-drying in detail proceeds as follows:
Lowering the temperature to +1° C., lowering the temperature to −40° C., turning on the vacuum, heating the trays to +40° C. and drying with full vacuum.

7. Sterilization

Sterilization was effected by radiation sterilization with 2.5 Mrad.

Example 3: Cultivation of Fibroblasts on the Flexible and Bio-Compatible Repair Patch In order to determine cell viability during cultivation of fibroblasts on the repair patch of the present invention the human dermal fibroblast cell line WS 1 was used. This cell line was grown under standard conditions (37° C., 5% $CO_2$) in Dulbecco's Modified Eagle Medium (DMEM) and 10% of fetal calf serum (FCS).

The fibroblasts were transferred to the repair patch of the present invention and a reference material and were cultivated over a time period of up to 5 weeks under standard conditions (37° C., 5% $CO_2$) in DMEM. To determine the cell proliferation rate WST 1 assays were used. This assay is a colorimetric assay for measuring the activity of cellular enzymes that reduce a tetrazolium dye, WST 1, to its insoluble formazan, giving a purple color. In addition, medium samples were analyzed by ELISA to determine their pro-collagen type I concentrations. Cell viability was analyzed once a week by live/dead cell staining under a fluorescence microscope.

For the in vitro testing of the repair patch of the present invention, fibroblasts were seeded on its surface. Cells were incubated under standard culture conditions for 14 days in a serum-free medium. After 3, 7 and 14 days cell viability and the de-novo synthesis rate of collagen type 1 were determined. A second collagen patch as well as a monolayer culture in cell culture plates served as controls.

The results revealed that the repair patch of the present invention is qualified for cell settlement. During the incubation time fibroblasts were able to survive on the patches and to synthesize pro-collagen type 1. Live/dead staining of fibroblasts resulted in a major proportion of living cells on the patches. Furthermore, an overgrowing of the surface could be determined specifically for the repair patch of the present invention. Compared to the monolayer reference, fibroblasts growing on the repair patch of the present invention showed an increase of metabolic activity as well as enhanced pro-collagen type 1 concentration levels after 14 days of incubation.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments. All documents cited herein, are hereby incorporated by reference in their entirety. The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. A method for repair of a damaged ligament or tendon at an injury site in a subject comprising:
applying a patch to said ligament or tendon so that the patch surrounds the ligament or tendon at the injury site and is fixed to the ligament or tendon, wherein
the patch is flexible and bio-compatible and comprises:
a support layer that is cell porous and consists of sheet collagen, and
a matrix layer disposed on the support layer, the matrix layer being a cell porous collagenous composite pad interspersed with (a) natural non-human collagen fibers having vacant spaces therebetween, and (b) natural hyaluronic acid that is present in a form selected from (i) natural hyaluronic acid fibers or (ii) hyaluronic acid powder in a gel or in a cream suspension dispersed into the vacant spaces between the non-human collagen fibers,
and wherein the patch allows migration of cells from the injury site to pass into the matrix layer.

2. The method of claim 1, wherein the support layer comprises porcine, bovine, or equine pericardial membrane or porcine split skin.

3. The method of claim 1, wherein the support layer comprises a dried porcine split skin layer.

4. The method of claim 1, wherein the cell porous collagenous composite pad of the matrix layer consists essentially of porcine, equine, bovine or vegetal collagen.

5. The method of claim 1, wherein the natural hyaluronic acid of the matrix layer consists essentially of natural, non-human hyaluronic acid.

6. The method of claim 5, wherein the natural, non-human hyaluronic acid of the matrix layer consists essentially of natural, non-human hyaluronic acid from a bacterial fermentation source.

7. The method of claim 1, wherein the matrix layer further comprises one or more compounds selected from analgesics, anti-inflammatory agents, antibiotics, and agents promoting either one or both of ligament and tendon regeneration.

8. The method of claim 7, wherein the agents promoting either one or both of ligament and tendon regeneration are selected from the group consisting of: growth factors, Diacerein, Rhein, chitosan and its derivatives, platelet rich plasma (PRP), and poly-lactic acid.

9. The method of claim 1, wherein the patch further comprises a third layer, which third layer is disposed on the matrix layer such that the matrix layer is sandwiched between the support layer and the third layer.

10. The method of claim 9, wherein the third layer is a collagen sheet layer.

11. The method of claim 9, wherein the third layer comprises porcine, bovine, or equine pericardial membrane or porcine split skin.

12. The method of claim 9, wherein the third layer is cell porous.

13. The method of claim 9, wherein the third layer comprises a dried porcine split skin layer.

14. The method of claim 1, wherein the patch has a thickness of 0.5 to 2 mm.

15. The method of claim 1, wherein the ligament or tendon is selected from (i) the group consisting of ligaments connected to the subject's head, neck, spine, thorax, pelvis, upper extremities, lower extremities, shoulder, elbow, wrist, hand, hip, knee, foot, and ankle, and (ii) the group consisting of tendons in the subject's upper extremities, lower extremities, shoulder, elbow, hands, hip, knee, feet, and ankle.

16. The method of claim 15, wherein
a) the ligament is selected from the group consisting of cricothyroid ligament, periodontal ligament, suspensory ligament of the lens, suspensory ligament of the breast, anterior sacroiliac ligament, posterior sacroiliac ligament, sacrotuberous ligament, sacrospinous ligament, inferior pubic ligament, superior pubic ligament, suspensory ligament of the penis, palmar radiocarpal ligament, dorsal radiocarpal ligament, ulnar collateral ligament, radial collateral ligament, acromio-clavicular ligament, coraco-clavicular ligament, cruciate ligament, anterior cruciate ligament (ACL), lateral collateral ligament (LCL), posterior cruciate ligament (PCL), medial collateral ligament (MCL), and patellar ligament; or
b) the tendon is selected from the group consisting of tendons connected to lower and upper extremities, tendons in the thoracic and abdominal area, spine, comprising head and neck, tendons of the hip and pelvic area, knee, foot and ankle, quadriceps tendon, and patellar tendon, tibialis ant. and post. tendons, peroneal tendons, Achilles tendon, extensor, flexor, abductor and adductor tendons of the foot and toes, tendons in the shoulder, elbow, and hand, rotator cuff tendons, subscapularis tendon, deltoid and pectoralis tendons, biceps brachii tendon, triceps brachii tendon, extensor, flexor, and abductor and adductor tendons of the hand and fingers.

17. The method of claim 1, wherein the subject is afflicted by a disorder affecting a ligament or tendon and comprising inflammation, autoimmune disease, infection, stress, strain, rupture, sprain, avulsion, overstretching, or tearing of the ligament or tendon.

18. The method of claim 1, wherein the patch is fixed to the ligament or tendon at the injury site by one or more of stitching, tying, suturing, welding or adhering with a glue.

19. The method of claim 18, wherein the patch is fixed to the ligament or tendon at the injury site with circular threads.

* * * * *